United States Patent [19]

Lahm et al.

[11] Patent Number: 5,686,393
[45] Date of Patent: Nov. 11, 1997

[54] ARTHROPODICIDAL OXAZOLINES AND THIAZOLINES

[75] Inventors: George Philip Lahm, Wilmington; Thomas Martin Stevenson, Newark, both of Del.

[73] Assignee: E. I. Du Pont de Nemours and Company, Wilmington, Del.

[21] Appl. No.: 586,797

[22] PCT Filed: Jul. 29, 1994

[86] PCT No.: PCT/US94/07459

§ 371 Date: Feb. 1, 1996

§ 102(e) Date: Feb. 1, 1996

[87] PCT Pub. No.: WO95/04726

PCT Pub. Date: Feb. 16, 1995

Related U.S. Application Data

[63] Continuation-in-part of Ser. No. 101,212, Aug. 4, 1993, abandoned, which is a continuation-in-part of Ser. No. 203,060, Feb. 28, 1994, abandoned.

[51] Int. Cl.⁶ .............. C07D 263/14; C07D 263/10; C07D 277/10; A01N 43/74
[52] U.S. Cl. .............. 504/270; 504/193; 504/235; 504/247; 504/252; 504/266; 514/63; 514/249; 514/307; 514/311; 514/340; 514/342; 514/365; 514/374; 544/353; 546/144; 546/167; 546/270.4; 546/271.4; 548/110; 548/146; 548/239
[58] Field of Search .............. 548/239; 514/374; 504/270

[56] References Cited

U.S. PATENT DOCUMENTS

| | | | |
|---|---|---|---|
| 3,901,906 | 8/1975 | Kozlik | 548/239 |
| 4,889,867 | 12/1989 | Lutomski et al. | 514/365 |
| 4,977,171 | 12/1990 | Suzuki et al. | 514/365 |
| 5,141,948 | 8/1992 | Miyamoto et al. | 514/365 |

FOREIGN PATENT DOCUMENTS

| | | | |
|---|---|---|---|
| 0 345 775 | 12/1989 | European Pat. Off. | C07D 263/10 |
| 0 432 661 | 6/1991 | European Pat. Off. | C07D 263/12 |
| 2-304069 | 12/1990 | Japan | C07D 263/10 |
| WO 93/22297 | 11/1993 | WIPO | C07D 263/14 |
| WO 93/24470 | 12/1993 | WIPO | C07D 263/10 |
| WO 93/25079 | 12/1993 | WIPO | A01N 43/76 |

OTHER PUBLICATIONS

Ardabilchi, N et al, *Chemical Abstracts*, 91(11), Abstract No. 91279r (1979).

Miyamoto, S. et al, *Chemical Abstracts*, 117(13), Abstract No. 131181s (1992).

Miyamoto, S. et al, *Patent Abstracts of Japan*, 16(13), Abstract No. C-0901 (1992).

*Primary Examiner*—Johann Richter
*Assistant Examiner*—Laura L. Stockton

[57] ABSTRACT

Described herein are arthropodicidal compounds, compositions and use of compounds of Formula (I) wherein the substituents are defined in the disclosure

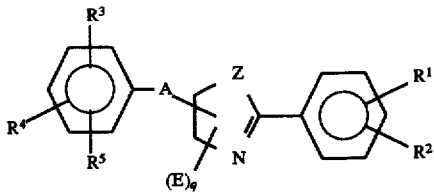

11 Claims, No Drawings

ARTHROPODICIDAL OXAZOLINES AND THIAZOLINES

This application is a 371 of PCT/US94/07459 filed Jul. 29, 1994 and a continuation-in-part of Ser. No. 08/101,212 filed Aug. 4, 1993, now abandoned, and a continuation-in-part of Ser. No. 08/203,060 filed Feb. 28, 1994, now abandoned.

The present invention comprises oxazolines and thiazolines useful as arthropodicides and acaricides. The arthropodicidal and acaricidal oxazolines and thiazolines of this invention are distinguished from those described in EP 345,775, EP 432,661, JP 489,484 and JP 2,304,069 by phenyl-ring substitution not disclosed by this art.

SUMMARY OF THE INVENTION

The invention comprises compounds of Formula I, including all geometric and stereoisomers, agriculturally suitable salts thereof, agricultural compositions containing them and their use as arthropodicides and acaricides in both agronomic and nonagronomic environments. The compounds are

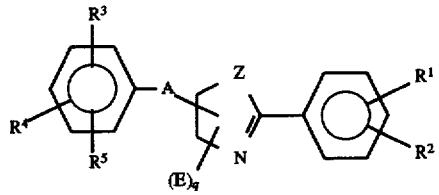

wherein:

A is selected from the group a direct bond and $C_1$-$C_3$ straight or branched chain alkylene;

E is selected from the group $C_1$-$C_4$ alkyl and $C_1$-$C_4$ haloalkyl;

Z is selected from the group O and S;

$R^1$ and $R^2$ are independently selected from the group H, halogen, $C_1$-$C_6$ alkyl, $C_1$-$C_6$ haloalkyl, $C_1$-$C_6$ haloalkoxy, $C_1$-$C_6$ alkylthio, CN and $NO_2$;

$R^3$ is selected from the group $C_3$-$C_7$ halocycloalkyl; $C_2$-$C_{10}$ haloalkenyl optionally substituted with at least one member independently selected from the group CN and $C_2$-$C_6$ alkoxycarbonyl; $C_1$-$C_{10}$ alkyl substituted with at least one member independently selected from the group $Si(R^6)(R^7)R^8$, CN, $C_2$-$C_6$ alkylcarbonyl, $C_2$-$C_6$ haloalkylcarbonyl, $C_2C_6$ haloalkoxycarbonyl, and $C_2$-$C_6$ alkoxycarbonyl; $C_2$-$C_6$ alkylcarbonyl; $C_2$-$C_{10}$ alkenyl optionally substituted with at least one member independently selected from $R^9$; $C_2$-$C_{10}$ alkynyl optionally substituted with at least one member independently selected from $R^9$; $C_2$-$C_6$ haloalkylcarbonyl; $C_2$-$C_6$ alkoxycarbonyl; $C_2$-$C_6$ haloalkoxycarbonyl; $C(O)R^9$; $C(O)OR^9$; $C(O)N(R^{10})R^{11}$; $OR^{12}$; tetrahydropyranyl; phenyl substituted with at least one member independently selected from $W^1$; and an 8- to 12-membered fused bicyclic ring system containing 0–4 heteroatoms independently selected from 0–4 nitrogen, 0–2 oxygen and 0–2 sulfur, the ring system optionally substituted with at least one member independently selected from W;

$R^4$ and $R^5$ are independently selected from the group H, halogen, CN, $NO_2$, $C_1$-$C_{16}$ alkyl, $C_1$-$C_{16}$ alkoxy, $C_1$-$C_{16}$ haloalkyl, $C_1$-$C_{16}$ haloalkoxy, $C_3$-$C_7$ cycloalkyl, $C_4$-$C_{16}$ cycloalkylalkyl, $C_2$-$C_{16}$ alkenyl, $C_2$-$C_{16}$ haloalkenyl, $C_2$-$C_{16}$ alkynyl, $C_2$-$C_{16}$ haloalkynyl, $C_2$-$C_{16}$ alkoxyalkoxy, $Si(R^6)(R^7)R^8$, and phenyl optionally substituted with at least one member independently selected from W;

$R^6$, $R^7$ and $R^8$ are independently selected from $C_1$-$C_6$ alkyl;

$R^9$ is selected from the group phenyl and pyridyl, each optionally substituted with at least one member independently selected from W;

$R^{10}$ and $R^{11}$ are independently selected from the group H, $C_1$-$C_6$ alkyl, $C_1$-$C_6$ haloalkyl, and phenyl optionally substituted with at least one member independently selected from W;

$R^{12}$ is selected from the group tetrahydropyranyl; $C_1$-$C_{10}$ alkyl substituted with at least one member independently selected from the group CN, $C_2$-$C_6$ alkylcarbonyl, $C_2$-$C_6$ haloalkylcarbonyl, $C_2$-$C_6$ haloalkoxycarbonyl, $C_2$-$C_6$ alkoxycarbonyl, $C_2$-$C_6$ alkylcarbonyl, and $Si(R^6)(R^7)R^8$; $C_3$-$C_7$ cycloalkyl; $C_3$-$C_7$ halocycloalkyl; $C_3$-$C_7$ cyanocycloalkyl; $C_4$-$C_7$ alkylcycloalkyl; $C_4$-$C_7$ cycloalkylalkyl; $C_4$-$C_7$ halocycloalkylalkyl; $C_3$-$C_{10}$ haloalkynyl; $C_2$-$C_{10}$ haloalkenyl optionally substituted with at least one member independently selected from the group CN and $C_2$-$C_6$ alkoxycarbonyl; and an 8- to 12-membered fused bicyclic ring system containing 0–4 heteroatoms independently selected from 0–4 nitrogen, 0–2 oxygen and 0–2 sulfur, the ring system optionally substituted with at least one member independently selected from W;

$R^{13}$ is selected from the group $C_1$-$C_3$ alkyl and $C_1$-$C_3$ haloalkyl;

W is selected from the group halogen, CN, CHO, $NO_2$, $SF_5$, $C_1$-$C_3$ alkyl, $C_1$-$C_3$ haloalkyl, $C_1$-$C_3$ alkylthio, $C_1$-$C_3$ alkoxy, $C_1$-$C_3$ haloalkoxy, $C_2$-$C_4$ alkylcarbonyl and $C_2$-$C_4$ alkoxycarbonyl;

$W^1$ is selected from the group CN, CHO, $NO_2$, $SF_5$, $S(O)_nR^{13}$, $C_2$-$C_4$ alkylcarbonyl, and $C_2$-$C_4$ alkoxycarbonyl;

n is 0, 1 or 2; and q is 0, 1, 2 or 3.

Preferred Compounds A are compounds of Formula I wherein

A is a direct bond;

$R^1$ is selected from the group F and Cl in the 2-position;

$R^2$ is selected from the group H, F and Cl in the 6-position;

$R^3$ is selected from the group $OR^{12}$, $C_2$-$C_{10}$ alkynyl optionally substituted with at least one member independently selected from $R^9$, phenyl substituted with at least one member independently selected from $W^1$, and an 8- to 12-membered fused bicyclic ring system containing 0–4 heteroatoms independently selected from 0–4 nitrogen, 0–2 oxygen and 0–2 sulfur, the ring system optionally substituted with at least one member independently selected from W.

Preferred Compounds B are compounds of Preferred A wherein $R^3$ is $OR^{12}$; and $R^{12}$ is $C_3$-$C_7$ cycloalkyl.

Preferred Compounds C are compounds of Preferred A wherein $R^3$ is $C_2$-$C_{10}$ alkynyl optionally substituted with at least one member independently selected from $R^9$.

Preferred Compounds D are compounds of Preferred A wherein $R^3$ is phenyl substituted with at least one member independently selected from $W^1$.

Preferred Compounds E are compounds of Preferred A wherein $R^3$ is an 8- to 12-membered fused bicyclic ring system containing 0–4 heteroatoms independently selected from 0–4 nitrogen, 0–2 oxygen and 0–2 sulfur, the ring system optionally substituted with at least one member independently selected from W.

Specifically preferred for biological activity is Compound F of Preferred D which is:

4'-((2-(2,6-difluorophenyl)-4,5-dihydro-4-oxazolyl))((1,1'-biphenyl))4-carbonitrile.

Specifically preferred for biological activity is Compound G of Preferred E which is:

2-(2,6-difluorophenyl)-4,5-dihydro-4-[4-(2-naphthalenyl)phenyl]oxazole.

Compounds of this invention can exist as one or more stereoisomers. The various stereoisomers include enantiomers, diastereomers and geometric isomers. One skilled in the art will appreciate that one stereoisomer may be more active than the others and how to separate stereoisomers. Accordingly, the present invention comprises racemic and optically active compound(s). The term optically active compound(s) includes individual stereoisomers, mixtures of stereoisomers enriched in one stereoisomer, and optically active mixtures of compounds.

The term "fused bicyclic ring system" is defined as those ring systems which satisfy the Hackel rule, including 8- to 12-membered fused bicyclic ring systems containing 0 to 4 heteroatoms and 1 or 2 aromatic rings, examples include naphthyl, tetralinyl, quinolyl, isoquinolyl, quinoxalinyl, benzofuryl, isobenzofuranyl, benzothienyl, benzodioxolyl, benzoxazolyl, chromanyl, indolinyl, isoindolyl, thienofuranyl, and purinyl. The aromatic ring systems can be attached through any available carbon or nitrogen, for example, for naphthyl, the bicyclic aromatic ring system si 1-naphthyl or 2-naphthyl, for benzofuryl, the aromatic ring system can be 2-, 3-, 4-, 5-, 6-, or 7-benzofuryl, and similarly for the other bicyclic ring systems.

In the above recitations, the term "alkyl" used either alone or in compound words such as "alkylthio" or "haloalkyl", denotes straight or branched alkyl such as methyl, ethyl, n-propyl, isopropyl and the different butyl, pentyl and higher isomers.

Alkoxy denotes methoxy, ethoxy, n-propyloxy, isopropyloxy and the different butoxy, pentoxy, hexyloxy and higher isomers. Alkenyl denotes straight or branched chain alkenes such as vinyl, 1-propenyl, 2-propenyl and the different butenyl, pentenyl, hexenyl and higher isomers. Alkynyl denotes straight chain or branched alkynes such as ethynyl, 1-propynyl, 3-propynyl and the different butynyl, pentynyl, hexynyl, and the higher isomers. Cycloalkyl denotes cyclopropyl, cyclobutyl, cyclopentyl, cyclohexyl and cycloheptyl. Cyanocyloalkyl denotes the carbocyclic rings above substituted by cyano. Alkylcycloalkyl denotes the above carbocyclic rings substituted with a straight or branch-chained alkyl group. Cycloalkylalkyl denotes a straight or branch-chained alkyl group substituted by cyclopropyl, cyclobutyl, cyclopentyl or cyclohexyl. Alkoxyalkoxy denotes alkoxy substitution on alkoxy. Alkylcarbonyl denotes carbonyl with an attached straight or branch-chained alkyl group. Alkoxycarbonyl denotes carbonyl with an attached straight or branch-chained alkoxy group.

The term "halogen", either alone or in compound word such as "haloalkyl", denotes fluorine, chlorine, bromine or iodine. Further, when used in compound words such as "haloalkyl", said alkyl can be partially or fully substituted with independently selected halogen atoms. Examples of haloalkyl include $CH_2CH_2F$, $CF_2CF_3$ and $CH_2CHFCl$. The terms "haloalkenyl" and "haloalkynyl" are defined analogously to the term "haloalkyl".

The total number of carbon atoms in a substituent group is indicated by the "$C_i$–$C_j$" prefix where i and j are numbers from 1 to 16. For example, $C_4$ alkoxyalkoxy designates the various isomers of an alkoxy group substituted with a second alkoxy group containing a total of 4 carbon atoms, examples including $OCH_2OCH_2CH_2CH_3$ and $OCH_2CH_2OCH_2CH_3$.

When a compound is substituted with a substituent bearing a subscript that indicates the number of said substituents can exceed 1, said substituents (when they exceed 1 ) are independently selected from the group of defined substituents.

DETAILS OF THE INVENTION

Compounds of Formula I can be made from amino alcohols (or thiols) of Formula II and benzoic acid derivatives as shown in Scheme 1 (in Schemes 1–8, Q is defined as a phenyl ring optionally substituted as defined above with $R^3$, $R^4$ and $R^5$). The transformation generally consists of two steps. First, the compound of Formula II is condensed with the benzoic acid derivative to form an amide of Formula III. A generally useful way to do this is to treat the compound of Formula II with an aroyl chloride in the presence of an acid acceptor (usually a tertiary amine base such as triethylamine) at room temperature or below. This reaction can be carried out in an inert solvent such as dichloromethane, tetrahydrofuran, toluene, and other solvents that will not react with acid chlorides or bases. There are other useful ways to form amides, many examples of which are found in Larock, "Comprehensive Organic Transformations," VCH New York, pp 972–981. The second step carried out is the ring closure. This can be accomplished by treating the intermediate amide of Formula III with a dehydrating agent. Some useful reagent systems for this transformation include but are not limited to triphenyl phosphine/carbon tetrachloride, diethylazodicarboxylate/triphenyl phosphine, and thionyl chloride. An especially useful method for ring closure involves treatment of the amide with thionyl chloride in benzene or other inert solvent at reflux until the starting material is consumed (usually 30 min to 3 h). The residue of this reaction is treated with an inorganic base such as sodium or potassium hydroxide in an alcoholic or aqueous medium (usually heating to reflux for 30 min to 2 h is required). Many methods for ring closure to oxazolines have been compiled by Frump (Chemical Rev. (1971) 71, 483–505).

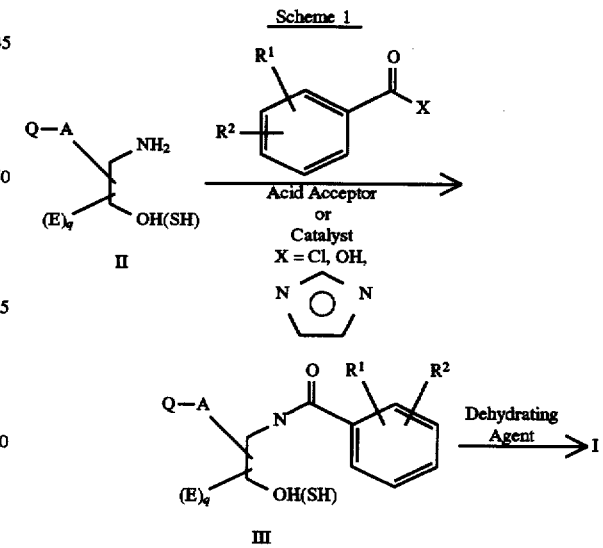

Alternatively, compounds of Formula III (where A is a direct bond) can be prepared in two steps as shown in Scheme 2. First, compounds of Formula IV are amidoalkylated with a compound of Formula V to form Formula VI compounds. A typical reaction involves the combination of compounds of Formulae IV and V in an acid such as sulfuric acid, methanesulfonic acid, trifluoroacetic acid, polyphosphoric acid and perchloric acid. The reaction can be run in a cosolvent such as acetic acid. The reaction temperature can range from −10° to 200° C. with 0°–100° C. being preferred. Alternatively, the reaction can be carried out in an inert solvent such as chloroform, methylene chloride, benzene, toluene and ether in the presence of a Lewis acid such as aluminum chloride or boron trifluoride. The acid, temperature, and time of the reaction vary according to the relative reactivity of the Q group towards electrophilic substitution reactions. Amidoalkylation reactions have been extensively reviewed in the literature (see Zaugg, *Synthesis* (1984) 85–110). The second step is the reduction of a Formula VI compound to form a Formula III compound. Reductions of this type are well-known in the art (see Hudlicky, *Reductions in Organic Chemistry* (1984) 136–163). Typical reducing agents include the alkali metal borohydrides and diborane. When V is a lower alkyl group, the use of lithium borohydride as reducing agent, tetrahydrofuran as solvent and performance of the reactions at 65° C. for 1–6 h, is preferred.

Scheme 2

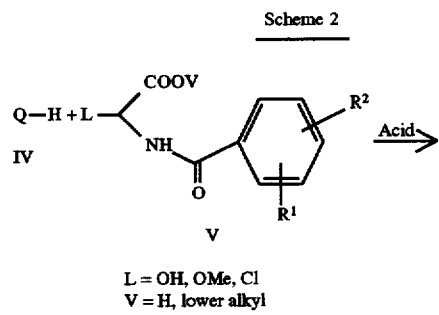

L = OH, OMe, Cl
V = H, lower alkyl

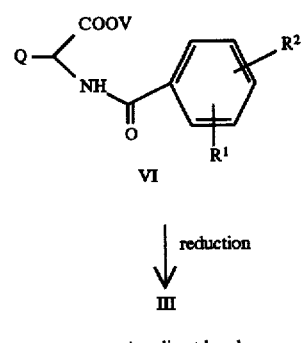

A = direct bond

The preparation of Formula V compounds can be accomplished by refluxing glyoxylic acid derivatives (Formula VII) and commercially available benzamides (Formula VIII) in an inert solvent such as acetone, benzene and chloroform (Scheme 3). This procedure is known in the art (see Ben-Ishai, *Tetrahedron* (1975) 31, 863–866 and *Tetrahedron* (1977) 33, 881–883).

Scheme 3

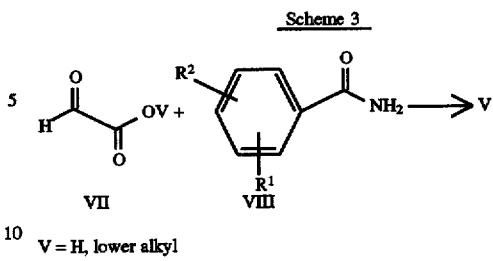

V = H, lower alkyl

As shown in Scheme 4, amino alcohols of Formula II can be produced by the treatment of an amino acid derivative of Formula IX with a reducing agent. In the reduction process, aminoesters are preferred, but amino acids themselves can also be used. There are many reagents known to reduce acids and esters to alcohols. (See Larock, loc. cit., pp 548–553). Particularly useful are alkali metal hydrides and boranes. For example, treatment of a compound of Formula IX with lithium aluminum hydride at 0°–50° C. in ethereal solvents such as tetrahydrofuran, ether, or dimethoxyethane gives an alcohol of Formula II.

Scheme 4

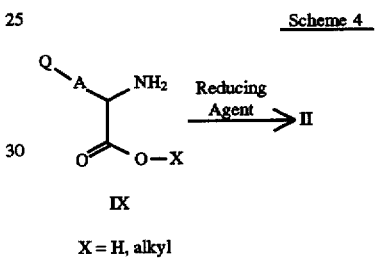

X = H, alkyl

As shown in Scheme 5, amino alcohols of Formula II can be produced by the direct reduction of oximo acids and esters of Formula X with boranes or alkali metal hydrides. The reaction conditions with lithium aluminum hydride are as described for Scheme 4.

Scheme 5

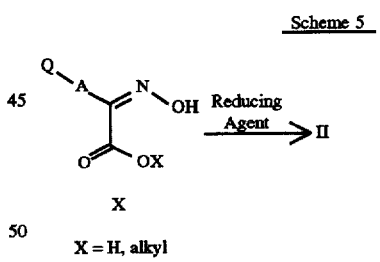

X = H, alkyl

Aryl-substituted amino acids and esters of Formula IX are known in the art as are methods for their preparation. Useful compendia of methods for their synthesis are contained in Kukolja (*J. Med. Chem.* (1985) 28, 1886–1896), Bohme (*J. Med. Chem.* (1980) 23, 405–412), and O'Donnell (*Tetrahedron Lett.* (1989) 30, 3909–3912) and references cited within.

Oximo esters of Formula X are especially suitable intermediates for the synthesis of compounds of Formula I. They can be made from aryl acetic esters of Formula XI by reaction, in the presence of base, with nitrosating agents such as inorganic and organic nitrites as shown in Scheme 6. Typically, the compound of Formula VI is treated with an alkyl nitrite such as butyl nitrite in an alcoholic solvent such as ethanol in the presence of a strong base such as sodium ethoxide at the reflux temperature of the solvent.

Scheme 6

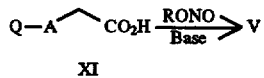

XI

X = alkyl, H
R = alkyl, H

Alternatively, as shown in Scheme 7, compounds of Formula X can be produced from aryl glyoxalates of Formula XII by treatment with a derivative of hydroxylamine. Aryl glyoxalates can be made by the reaction of an organometallic species with a derivative of oxalic acid. For instance, diethyl oxalate can be treated with an aryl grignard reagent at low temperature in ether/tetrahydrofuran mixtures (Rambaud, et al., *Synthesis* (1988) 564–567).

Scheme 7

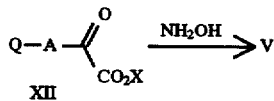

XII

X = H, alkyl

Another method for the synthesis of compounds of Formula XII, shown in Scheme 8, is by use of the Friedel-Crafts reaction. Monoesters of oxalyl chloride react with electron-rich aromatics of Formula XIII in the presence of Lewis acids to give compounds of Formula XII. See Olah Ed., "*Friedel-Crafts and Related Reactions,*" Vol. 3, Part 1, pp 1–16. Treatment of compounds of Formula XIII with aluminum chloride and ethyl or methyloxalyl chloride in an inert solvent such as dichloromethane, nitrobenzene, carbon disulfide, or dichloroethane will produce compounds of Formula XII.

Scheme 8

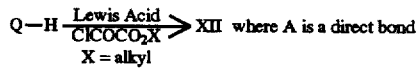

Compounds of Formula I in which $R^3$=$OR^{12}$ can be synthesized as shown in Scheme 9. A compound of Formula XIII may be alkylated by a substituted alkylhalide or sulfonate XIV in the presence of an acid acceptor. The reaction can be carded out in a variety of inert polar aprotic solvents such as acetonitrile, dimethylformamide, dimethylacetamide, dimethylsulfoxide, and 2-butanone. Suitable acid acceptors include both organic and inorganic bases such as alkali hydrides, carbonates, and hydroxides. A preferred base and solvent combination is potassium carbonate in dimethylformamide. The process can be carried out from 0°–150° C., preferably at 25° C.

Scheme 9

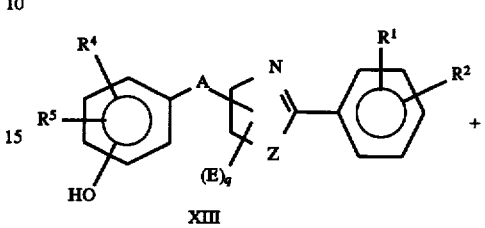

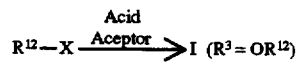

XIV

X = halide, sulfonate

Compounds of Formula I containing an ester, amide or ketone function as $R^3$ can be synthesized by palladium catalyzed carbonylation of compounds of Formula I containing sulfonates or halides as shown in Scheme 10. To synthesize amides and esters the compound of Formula XV is treated with an alcohol XVI or amine XVII under an atmosphere of carbo monoxide in the presence of a palladium catalyst and a phosphine ligand in a dipolar aprotic solvent such as dimethyl sulfoxide or dimethylformamide. The reaction can be carried out at 25°–120° C. and preferably at 65°–70° C. for 2–5 h. The preferred catalyst system is palladium acetate and diphenylphosphinopropane. Leading references for this transformation are found in *Tetrahedron Lett.* (1992) 33, 1959–1962. If the above mentioned process is carried out in the presence of an organotin compound XVIII instead of alcohol or amine, the product is a ketone ($R^3$=$C_2$–$C_6$ alkylcarbonyl or C(O)$R^9$). The utility of organotin compounds in ketone synthesis has been reviewed see *Synthesis* (1992) 803–815 and *Angewandte Chemie.*, Int. Ed. Engl. (1986) 25, 508–524. Organoboron compounds can also be used to make ketones; see Ishiyama et. al. *Tetrahedron Lett.* (1993) 34, 7595–7598 and references cited therein.

Scheme 10

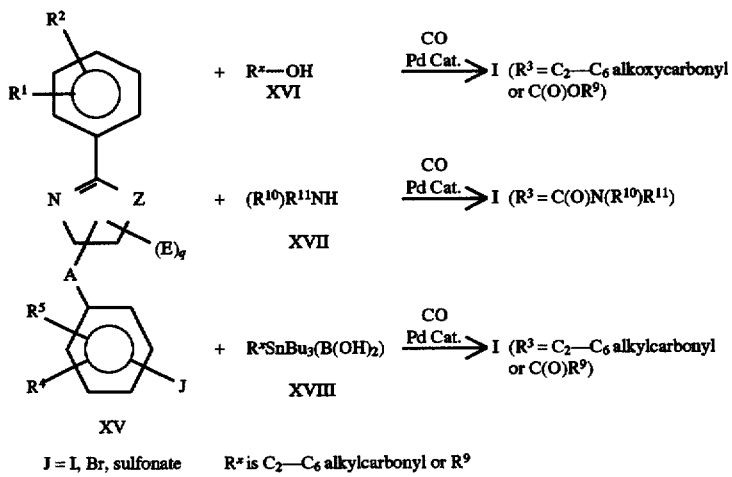

J = I, Br, sulfonate    R* is C$_2$—C$_6$ alkylcarbonyl or R$^9$

Organometallic coupling reactions can also be used to introduce other R$^3$ substituents as shown in Scheme 11. Organometallic reagents can be coupled with compounds of Formula XV with palladium, copper, or nickel catalysis. The organometallic reagent XIX can be chosen from a wide variety of metals including tin, zinc, magnesium, and boron. Tamao has summarized a range of different catalysts and conditions for these coupling reactions in *Comprehensive Organic Synthesis;* B. M. Trost Ed., Pergamon, (1991) Vol. 3, 435–520. Specific conditions and reactions of heterocyclic compounds in palladium and nickel catalyzed coupling reactions can be found in Kallinin, *Synthesis* (1992) 413–432. The synthesis of XIX (where Met is Zinc) can be accomplished in many ways, and a review of these conditions and procedures can be found in Knochel, *Chemical Reviews* (1993) 93, (2117–2188). The synthesis of XIX (where Met is Sn) is found in *Synthesis* (1992) 803–815 and *Angewandte Chemie., Int. Ed. Eng.* (1986) 25, 508–524. The synthesis of XIX (where Met is B(OH)$_2$) is found in Ali et. al., *Tetrahedron*, (1992) 37, 8117–8126, and references cited therein. The starting materials for these compounds where R$^3$ is a fused bicyclic ring system are known. Methods for the synthesis of compounds containing heteroatoms in the bicyclic ring system is found in Katritsky and Rees Eds., "*Comprehensive Heterocyclic*" Vol. 2–6 Pergamon, New York, (1984) and in Coffey Ed., "*Rodd's Chemistry of the Carbon Compounds*" Vol. IV a–1, Elsever, Amsterdam, (1973–1980). The chemistry of other bicyclic ring systems can be found in European Patent Publication EP-A-350,846; Berlin et. al., *J. Med. Chem.*, (1985) 28, 116–124; Dawson et. al., *J. Med Chem.* (1984) 27, 1516–1531 and Olah, loc. cit., Vol. 2, 785–952. The chemistry and synthesis of naphthalenes is known and can be found in Coffey, loc. cit., Vol. III q, 99–284.

Scheme 11

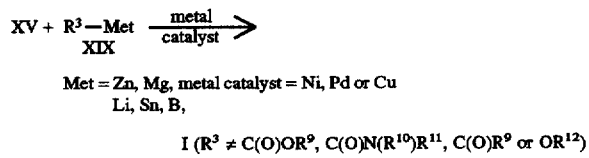

Met = Zn, Mg, metal catalyst = Ni, Pd or Cu
Li, Sn, B,

I (R$^3 \neq$ C(O)OR$^9$, C(O)N(R$^{10}$)R$^{11}$, C(O)R$^9$ or OR$^{12}$)

Compounds in which R$^3$ is alkenyl or alkynyl optionally substituted with R$^9$ can be made as shown in Scheme 12.

Compounds of Formula XV can react with alkenes (XX) or alkynes (XXI) in the presence of palladium catalysts. This sequence is known as the Heck reaction and has been discussed in great detail by Heck in "*Palladium Reagents in Organic Synthesis*"; Academic, London, 1985. Other more recent modifications of this reaction are summarized in Larock and Baker, *Tetrahedron Lett.* (1988) 29, 905–908 and in Cabri et. al. *J. Org. Chem.* (1992) 57, 3558–3563. Typically, the compound of Formula XV and palladium acetate (1–5 mol %) and triphenyl phosphine (2–10 mol %) are heated with the alkene (XX) (1 to 3 equivalents) in dimethyl formamide or other aprotic solvents at 60°–120° C. The presence of a base such as triethylamine, sodium acetate, sodium carbonate or potassium carbonate is required. When an alkyne (XXI) is used, the presence of a catalytic amount of CuI (1–5 mol %) accelerates the reaction. In this case it is often preferable to carry out the reaction using an organic base (i.e. triethylamine) as the solvent. Under these conditions the reaction with alkynes (XXI) often proceeds without external heating.

Scheme 12

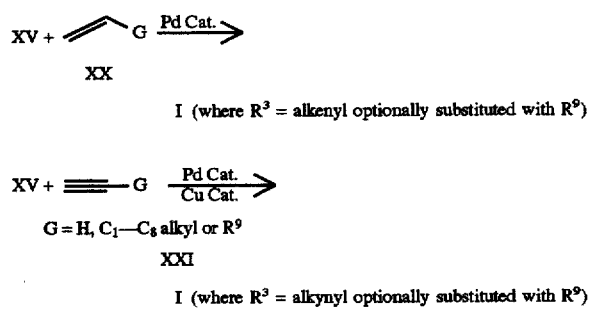

It is recognized that some reagents and reaction conditions described above for preparing compounds of Formula I may not be compatible with certain functionalities present in the intermediates. In these instances, the incorporation of protection/deprotection sequences into the synthesis will aid in obtaining the desired products. The use and choice of the protecting group will be apparent to one skilled in chemical synthesis.

EXAMPLE 1

2-(2,6-Difluorophenyl)-4,5-dihydro-4-(4-cyclopentyloxyphenyl) oxazole

Step A: Methyl[(2,6-difluorobenzoyl)amino]hydroxyacetate

A solution of glyoxylic acid monohydrate (37.2 g) was stirred in methanol (125 mL) and after 72 h the solvent was evaporated. The residue was dissolved in benzene (150 mL) and heated to reflux with 2,6-difluorobenzamide (44 g). After 16 h the cooled reaction mixture was diluted with benzene (100 mL) and filtered. Air drying left 64 g of crude product which was used without further purification: $^1$H NMR (CDCl$_3$, 200 MHz), δ 9.7 (1H), 7.5 (1H), 7.2 (2H), 6.9 (1H), 3.7 (3H).

Step. B: [(4-Cyclopentyloxy)-α-[(2,6-difluorobenzoyl)amino]benzenemethanol

Cyclopentyloxybenzene (4 g) was dissolved in trifluoroacetic acid (30 mL) treated with the compound of Step A (6.4 g) and stirred for 18 h at room temperature. The solvent was evaporated and the residue was partitioned between dichloromethane and saturated aqueous sodium bicarbonate. The organic layer was separated and dried. The residue was subjected to silica gel chromatography with hexanes/ethyl acetate (3:1 to 2:1) as eluent to give an oil (2.9 g). The oil was dissolved in tetrahydrofuran (20 mL) and treated with lithium borohydride (4.2 mL of 1N solution in tetrahydrofuran). The mixture was heated at reflux for 4 h. The cooled mixture was decomposed by the slow addition of 1N hydrochloric acid until the evolution of hydrogen ceased. The reaction was then diluted with water and extracted with dichloromethane. The residue was subjected to chromatography on silica gel with hexanes/ethyl acetate (2:1) as eluent. The first spot to elute was the ortho-cyclopentyloxy product. The second spot (1.5 g) was the 4-cyclopentyloxy product: $^1$H NMR (CDCl$_3$, 200 MHz), δ 7.3–6.9 (ArH), 6.7 (NH), 5.3 (1H), 4.8 (1H), 3.9 (2H), 2.2–1.7 (8H).

Step C: 4-[4-(Cyclopentyloxy)phenyl]-2-(2,6-difluorophenyl)-4,5-dihydrooxazole

The compound of Step B was dissolved in toluene (20 mL), treated with thionyl chloride (1.8 mL) and heated to reflux for 1 h. The solvent was evaporated and the residue was dissolved in methanol (25 mL). Sodium hydroxide (2 mL of 50% aqueous solution) was added and the mixture refluxed for 1 h. The solvent was evaporated and the residue partitioned between dichloromethane and water. The organic layer was separated, dried and evaporated. The residue was subjected to chromatography on silica gel with hexanes/ethyl acetate 5:1 as eluent to give the title compound (1.0 g) as an oil: $^1$H NMR (CDCl$_3$, 200 MHz), δ 7.3–6.9 (ArH), 5.4 (1H), 4.8 (2H), 4.3 (1H), 1.9–1.6 (8H).

EXAMPLE 2

2-(2,6-Difluorophenyl)-4,5-dihydro-4-(4-iodophenyl) oxazole

The compound of Step A of Example 1 (31.0 g, 0.13 mol) and iodobenzene (40.2 g, 0.19 mol) were suspended in sulfuric acid (100 mL) and stirred for 3 days at 23° C. The mixture was poured onto ice and extracted with dichloromethane (200 mL). The dichloromethane layer was dried over magnesium sulfate and evaporated under reduced pressure. Methanol (200 mL) and thionyl chloride (6 mL) were added and the mixture and heated at reflux for 30 min. The methanol was removed under reduced pressure and the residue was dissolved in tetrahydrofuran (200 mL). Lithium borohydride (55 mL, 2N in tetrahydrofuran, 0.11 mol) was added slowly and after completion of the addition, the mixture was heated at reflux for 1 h. The mixture was cooled, and quenched by slow addition of aqueous hydrochloric acid (200 mL, 1N). The mixture was extracted with dichloromethane (200 mL), dried over magnesium sulfate and evaporated under reduced pressure. The residue was then treated with toluene (100 mL) and thionyl chloride (23 mL, 0.3 mol). The mixture was heated to reflux for 45 min and then evaporated under reduced pressure. The residue was dissolved in methanol (200 mL) and treated with aqueous sodium hydroxide (30 mL, 50% solution). The mixture was heated to reflux for 30 min and then evaporated under reduced pressure. The residue was partitioned between water (100 mL) and dichloromethane (200 mL). The dichloromethane solution was dried over magnesium sulfate and evaporated under reduced pressure. The residue was subjected to column chromatography on silica gel using hexanes/ethyl acetate (10:1) as eluent to give the title compound (23.1 g) as a white solid: m.p.: 105°–106° C. $^1$H NMR (CDCl$_3$, 200 MHz) δ 7.7 (m,2H), 7.5 (m, 1H), 7.1 (m, 1H), 7.0 (m,2H), 5.4 (m, 1H), 4.8 (m, 1H), 4.3 (m, 1H).

EXAMPLE 3

2-(2,6-Difluorophenyl)4,5-dihydro-4-[4-(2-naphthylenyl) phenyl]-oxazole The compound of Example 2 (0.63 g, 0.17 mmol) and 2-naphthyl boronic acid (Tetrahedron, (1992), 8073, 0.5 g, 0.29 mmol) were suspended in a mixture of dimethoxyethane (10 mL) and saturated aqueous sodium bicarbonate (20 mL) and treated with bis (triphenylphosphine)palladium chloride (0.05 g, 0.07 mmol). The mixture was heated at reflux for 2 h. After cooling, water (50 mL) and dichloromethane (50 mL) were added and the dichloromethane was separated and dried over magnesium sulfate. The residue obtained after evaporation of the solvent was subjected to chromatography on silica gel with hexanes/ethyl acetate (8:1 to 6:1) as eluent to give the title compound (0.42 g) as a white solid: m.p.: 166° C. $^1$H NMR (CDCl$_3$, 200 MHZ) δ 8.1∝7.0 (m, 14H), 5.5 (m, 1H), 4.9 (m, 1H), 4.3 (m, 1H).

EXAMPLE 4

[4-[2-(2,6-Difluorophenyl)-4,5-dihydro-4-oxazolyl]-(4-fluorophenyl)methanone

The compound of Example 2 (0.5 g, 1.3 mmol) and 4-fluorophenyl boronic acid (0.27 g, 2 mmol) and potassium carbonate (fine mesh, 0.5 g, 0.4 mmol) were suspended in anisole (15 mL) and carbon monoxide was bubbled through the mixture for 5 min. Bis (triphenylphosphine) palladium chloride (0.03 g, 0.50 mmol) was added and the mixture was evacuated and carbon monoxide was released into the reaction by means of a balloon. The evacuation and carbon monoxide release was repeated and the reaction was heated to 80° C. under a carbon monoxide atmosphere for 3 h. The anisole was removed under reduced pressure and the residue was partitioned between diethylether (50 mL) and water (50 mL). The ether solution was dried over magnesium sulfate and evaporated under reduced pressure. The residue was subjected to silica gel chromatography with hexanes/ethyl acetate (5:1) as eluent to give the title compound (0.34 g) as a solid: m.p.: 105°–106° C. $^1$H NMR (CDCl$_3$, 400 MHz) δ 7.9–7.0 (m, 1H), 5.6 (m, 1H), 4.9 (m, 1H), 4.3 (m, 1H).

EXAMPLE 5

2-(2,6-Difluorophenyl)-4-[4-[2-(4-fluorophenyl)ethenyl]phenyl]-4,5-dihydrooxazole The compound of Example 2 (0.7 g, 1.8 mmol), 4-fluorostyrene (1 g, 2.6 mmol), palladium acetate (0.03 g, 0.013 mmol) and tri-o-tolyphosphine (0.03 g, 0.01 mmol)

were heated to 100°–120° C. in dimethylformamide (20 mL). After 3 h, palladium acetate (0.03 g, 0.013 mmol) was added and heating was continued for 2 h. The cooled reaction mixture was extracted with diethylether (50 mL) and water (100 mL). The diethylether solution was dried over magnesium sulfate and evaporated under reduced pressure. The residue was subjected to chromatography on silica gel using hexanes/ethyl acetate (6:1) as eluent. The product was isolated as a solid (0.28 g): m.p.: 154°–156° C. $^1$H NMR (CDCl$_3$, 200 MHz) δ 7.5–7.0 (m, 13H), 5.5 (m, 1H), 4.8 (m, 1H), 4.3 (m, 1H).

EXAMPLE 6

4-[(2,6-Difluorophenyl)-4,5-dihydro-4-oxazolyl]phenol

The compound of Step A, Example 1 (51 g, 0.2 mol) and phenol (32 g 0.3 mol) were dissolved in trifluoroacetic acid (85 mL), stirred for 2 days and then evaporated under reduced pressure. The residue was taken up in dichloromethane (200 mL), washed with sodium bicarbonate solution, dried over magnesium sulfate and evaporated. The residue was subjected to chromatogaphy on silica gel using hexanes/ethyl acetate (2:1). The residue from the column (30 g) was dissolved in tetrahydrofuran (100 mL) and treated with lithium borohydride (60 mL, 2N in tetrahydrofuran) and heated at reflux for 3 h. The reaction mixture was treated with aqueous hydrochloric acid (1N, 300 mL) and extracted with dichloromethane (200 mL), dried and evaporated. The residue was treated with toluene (150 mL) and thionyl chloride (30 mL, 0.4 mol). After being heated at reflux for 1 h, the mixture was evaporated under reduced pressure. The residue was dissolved in methanol (200 mL) and treated with sodium hydroxide (20 mL, 50%) and heated at reflux for 1 h. The mixture was neutralized with aqueous hydrochloric acid and extracted with dichloromethane (200 mL). The dichloromethane was dried, evaporated, and subjected to chromatography on silica gel with hexanes/ethyl acetate (3:1 to 2:1). The second major fraction to elute was the title compound (7.7 g) as a white solid: m.p. 145°–147° C. $^1$H NMR (CDCl$_3$, 200 MHz) δ 9.3 (br s,OH), 7.7–6.8 (m,7H), 5.4 (m, 1H), 4.8 (m, 1H), 4.3 (m, 1H).

EXAMPLE 7

2-(2,6-Difluorophenyl)-4,5-dihydro-4-[4-(2-naphthalenylmethoxy)-phenyl]oxazole

The compound of Example 6 (0.36 g, 1.3 mmol) and 2-bromomethyl naphthalene (0.4 g, 1.7 mmol) were stirred at 23° C. for 18 h with potassium carbonate (0.6 g, 4 mmol) in dimethylformamide (10 mL). The mixture was poured into water (50 mL) and extracted with diethylether (50 mL). The diethylether was washed with water (50 mL) twice, dried over magnesium sulfate, and evaporated under reduced pressure. The residue was subjected to silica gel chromatography using hexanes/ethyl acetate (6:1) as eluent to give the title compound as a solid (0.27 g): m.p. 148°–150° C. $^1$H NMR (CDCl$_3$, 200 MHz) δ 7.8–7.0 (m, 14H), 5.4 (m, 1H), 5.2 (m,2H), 4.8 (m, 1H), 4.3 (m, 1H).

EXAMPLE 8

4-[2-(2,6-Difluorophenyl)-4,5-dihydro-4-oxazolyl]-N-(4-fluorophenyl)benzamide

The compound of Example 2 (1.0 g, 3 mmol) and 4-fluoroaniline (0.33 g, 3 mmol) were dissolved in dimethylsulfoxide (20 mL) and treated with triethylamine (1 mL) and bis (diphenylphosphino) propane (0.1 g, 2 mmol). Carbon monoxide was bubbled through the mixture for 5 min and palladium acetate (0.05 g, 2 mmol) was added. The mixture was evacuated with carbon monoxide was released into the reaction by means of a balloon. The evacuation and carbon monoxide release was repeated and the reaction was heated to 70° C. under a carbon monoxide atmosphere for 6 h. The compound, 4-floroaniline (0.33 g, 3 mmol), was added and heating continued for 1 h. The mixture was allowed to stand overnight and was added to water (100 mL). The solid form was filtered, taken up in a mixture of dichloromethane and ethyl acetate, and dried over magnesium sulfate. The residue, after evaporation under reduced pressure, was subjected to chromatography on silica gel with hexanes/ethyl acetate (3:1 to 1:2) as eluent. The title compound (0.45 g) was a slightly orange solid: m.p. 210°–212° C. $^1$H NMR (DMSO-D$_6$, 200 MHz) δ 10.4 (b s,NH), 8.0–7.2 (m,11H), 5.6 (m, 1H), 4.8 (m, 1H), 4.3 (m, 1H).

EXAMPLE 9

2-(2,6-Difluorophenyl)-4-[4-[(4-chlorophenyl)ethynyl] phenyl]-4,5-dihydro-oxazole Step A: 2-(2,6-Difluorophenyl)-4-ethynylphenyl]-4,5-dihydro-oxazole The compound of Example 2 (25 g, 64 mmol), trimethylsilylacetylene (16 mL, 110 mmol), bis (triphenylphosphine) palladium dichloride (0.5 g, 0.7 mmol), and copper(I)iodide (0.22 g, 1.1 mmol) were mixed together in triethylamine (200 mL). The reaction mixture slowly exothermed to 65° C. over 30 min and then slowly cooled to room temperature. After 2 h the mixture was evaporated and partitioned between dichloromethane (200 mL) and water (400 mL). The dichloromethane was washed with water (200 mL) and dried over magnesium sulfate. The residue after evaporation of solvent was dissolved in methanol (200 mL) and treated with sodium hydroxide (10 mL, 50% in water). The reaction was stirred at room temperature for 30 min. The methanol was evaporated and the residue was partitioned between water (500 mL) and dichloromethane (300 mL). The dichloromethane was dried over magnesium sulfate and evaporated. The residue was subjected to chromatography on silica gel in hexanes/ethyl acetate (5:1 to 3:1 ) to afford the desired material as an oil (7.2 g). $^1$H NMR (CDCl$_3$, 300 MHz) δ 7.5–7.0 (m,7H), 5.45 (m, 1H), 4.8 (m, 1H), 4.3 (m, 1H), 3.1 (m, 1H).

Step B: 2-(2,6-Difluorophenyl)-4-[4-[(4-chlorophenyl) ethynyl]phenyl]-4,5-dihydro-oxazole The compound of Step A (0.7 g, 2.5 mmol), 4-chloro-iodobenzene (0.7 g, 3 mmol), bis(triphenylphosphine) palladium dichloride (0.04 g, 0.06 mmol), and copper(I) iodide (0.04 g, 0.12 mmol) were mixed in triethylamine (6 mL). The reactants were stirred at 23 ° C. for 18 h and the solvent was evaporated. The residue was partitioned between water (100 mL) and dichloromethane (100 mL). The dichloromethane was dried over magnesium sulfate and evaporated. The residue was chromatographed on silica gel with hexanes/ethyl acetate (5:1 to 3:1) as eluent to give the title compound (0.56 g) as a yellow solid: m.p.: 155°–156° C., $^1$H NMR (CDCl$_3$, 300 MHz) δ 7.6–7.0 (m, 11H), 5.5 (m, 1H), 4.8 (m, 1H), 4.3 (m, 1H).

EXAMPLE 10

2-(2,6-Difluorophenyl)-4-[(4-phenyl)ethynylphenyl]-4,5-dihydro-oxazole

The compound of Example 2 (0.7 g, 1.8 mmol), phenylacetylene (1 mL, 9 mmol), bis(triphenylphosphine) palladium dichloride (0.05 g, 0.07 mmol), and copper(I) iodide (0.02 g, 0.06 mmol) were mixed in triethylamine (6 mL). The reactants were stirred at 23° C. for 18 h and the solvent was evaporated. The residue was partitioned between water (100 mL) and dichloromethane (100 mL). The dichloromethane was dried over magnesium sulfate and evaporated. The residue was chromatographed on silica gel with hexanes/ethyl acetate (9:1) as eluent to give the title compound (0.55 g) as an oil. $^1$H NMR (CDCl$_3$, 300 Mhz) δ 7.6–7.0 (m, 12H), 5.5 (m, 1H), 4.8 (m, 1H), 4.3 (m, 1H).

EXAMPLE 11

4'-[2-(2,6-Difluorophenyl)-4,5-dihydro-4-oxazolyl][1,1'-biphenyl]-4-carbonitrile The compound of Example 2 (6.5 g, 17 mmol) and bis(triphenylphosphine) palladium dichloride (0.15 g, 0.45 mmol) were dissolved in tetrahydrofuran (60 mL). The compound 4-cyanophenylzinc bromide (Rieke Organometallics, Lincoln, Nebr., 0.28 M in tetrahydrofuran, 72 ml) was added over 2 min and the mixture was stirred at 25° C. for 18 h. The reaction mixture was diluted with water (200 mL) and extracted with ether (100 mL). The aqueous layer was extracted with dichloromethane (100 mL) and the combined organic layers were dried over magnesium sulfate and evaporated. The residue was subjected to silica gel chromatography with hexanes/ethyl acetate 5:1 as eluent. The title compound was isolated as a yellow solid (4.5 g): m.p. 136°–138° C. $^1$H NMR (CDCl$_3$, 300 MHz) δ 7.8–7.0 (11H), 5.6 (1H), 4.9 (1H), 4.3 (1H)

By the procedures described herein the following compounds of Tables 1, 2, 3, 4 and 5 can be prepared. The compounds in Table 1, line 1 can be referred to as 1-1-1 and 1-1-2 (as designated by Table, line and column). All the other specific compounds covered in these Tables can be designated in an analogous fashion. The following abbreviations have been used in Tables 1, 2, 3, 4 and 5: Me=methyl, Et=ethyl, Pr=n-propyl, i-Pr=isopropyl and Ph=phenyl.

Key Structure for Tables 1, 2, 3, 4 and 5

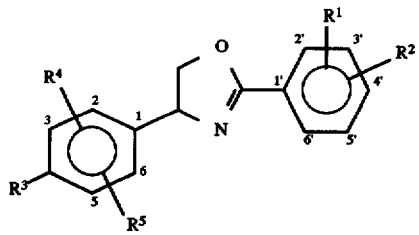

TABLE 1

$R^1$=2'-F, $R^2$=6'-F, $R^4$=H, $R^5$=H, $R^3$=

| | COLUMN 1 | COLUMN 2 |
|---|---|---|
| 1 | 2,2-dichlorocyclopropyl | 2,2,3,3-tetrafluorocyclobutyl |
| 2 | 2-chloro-2-propenyl | 2,2-dichloroethenyl |
| 3 | CH$_2$SiMe$_3$ | CH$_2$CH$_2$CN |
| 4 | CH$_2$CH$_2$CH$_2$CN | CH$_2$CH$_2$C(O)OMe |
| 5 | CH$_2$CH$_2$CH$_2$C(O)OEt | (CH$_2$)$_6$C(O)OMe |
| 6 | OCH$_2$SiMe$_3$ | O(CH$_2$)$_3$SiMe$_3$ |
| 7 | CH$_2$C(O)CH$_3$ | CH$_2$C(O)CF$_3$ |
| 8 | OCH$_2$CN | OCH$_2$CH$_2$CN |
| 9 | O(CH$_2$)$_3$CN | O(CH$_2$)$_4$CN |
| 10 | O(CH$_2$)$_6$CN | OCH$_2$C(O)OMe |
| 11 | OCH$_2$C(O)OEt | OCH$_2$C(O)OPr |
| 12 | OCH$_2$C(O)O-i-Pr | OCH$_2$CH$_2$C(O)OMe |

TABLE 1-continued $R^1$=2'-F, $R^2$=6'-F, $R^4$=H, $R^5$=H, $R^3$=

| | COLUMN 1 | COLUMN 2 |
|---|---|---|
| 13 | OCH$_2$CH$_2$C(O)OEt | O(CH$_2$)$_3$C(O)OMe |
| 14 | O(CH$_2$)$_3$C(O)OEt | O(CH$_2$)$_4$C(O)OMe |
| 15 | O(CH$_2$)$_5$C(O)OEt | O(CH$_2$)$_5$C(O)OMe |
| 16 | OCH$_2$C(O)OCH$_2$CF$_3$ | C(O)OMe |
| 17 | C(O)OEt | C(O)O-n-Pr |
| 18 | C(O)O-i-Pr | C(O)OPh |
| 19 | C(O)NMe$_2$ | C(O)NHPh |
| 20 | C(O)NH-i-Pr | C(O)N(Me)Ph |
| 21 | C(O)NH(CH$_2$)$_4$CH$_3$ | C(O)Me |
| 22 | C(O)Et | C(O)(CH$_2$)$_3$CH$_3$ |
| 23 | C(O)Ph | C(O)-4-Cl—Ph |
| 24 | 2-tetrahydropyranyl | cyclopropyloxy |
| 25 | cyclobutyloxy | cyclopentyloxy |
| 26 | cyclohexyloxy | cycloheptyloxy |
| 27 | OCH$_2$-cyclopropyl | OCH$_2$-cyclopentyl |
| 28 | OCH$_2$C(Cl)=CH$_2$ | OCH$_2$C=C—Br |
| 29 | OCH$_2$CH=C(Cl)$_2$ | OCH$_2$C(Br)=CH$_2$ |

TABLE 2

$R^1$=2'-Cl, $R^2$=6'-F, $R^4$=H, $R^5$=H, $R^3$=

| | COLUMN 1 | COLUMN 2 |
|---|---|---|
| 30 | 2,2-dichlorocyclopropyl | 2,2,3,3-tetrafluorocyclobutyl |
| 31 | 2-chloro-2-propenyl | 2,2-dichloroethenyl |
| 32 | CH$_2$SiMe$_3$ | CH$_2$CH$_2$CN |
| 33 | CH$_2$CH$_2$CH$_2$CN | CH$_2$CH$_2$C(O)OMe |
| 34 | CH$_2$CH$_2$CH$_2$C(O)OEt | (CH$_2$)$_6$C(O)OMe |
| 35 | OCH$_2$SiMe$_3$ | O(CH$_2$)$_3$SiMe$_3$ |
| 36 | CH$_2$C(O)CH$_3$ | CH$_2$C(O)CF$_3$ |
| 37 | OCH$_2$CN | OCH$_2$CH$_2$CN |
| 38 | O(CH$_2$)$_3$CN | O(CH$_2$)$_4$CN |
| 39 | O(CH$_2$)$_6$CN | OCH$_2$C(O)OMe |
| 40 | OCH$_2$C(O)OEt | OCH$_2$C(O)OPr |
| 41 | OCH$_2$C(O)O-i-Pr | OCH$_2$CH$_2$C(O)OMe |
| 42 | OCH$_2$CH$_2$C(O)OEt | O(CH$_2$)$_3$C(O)OMe |
| 43 | O(CH$_2$)$_3$C(O)OEt | O(CH$_2$)$_4$C(O)OMe |
| 44 | O(CH$_2$)$_5$C(O)OEt | O(CH$_2$)$_5$C(O)OMe |
| 45 | OCH$_2$C(O)OCH$_2$CF$_3$ | C(O)OMe |
| 46 | C(O)OEt | C(O)O-n-Pr |
| 47 | C(O)O-i-Pr | C(O)OPh |
| 48 | C(O)NMe$_2$ | C(O)NHPh |
| 49 | C(O)NH-i-Pr | C(O)N(Me)Ph |
| 50 | C(O)NH(CH$_2$)$_4$CH$_3$ | C(O)Me |
| 51 | C(O)Et | C(O)(CH$_2$)$_3$CH$_3$ |
| 52 | C(O)Ph | C(O)$_4$-Cl—Ph |
| 53 | 2-tetrahydropyranyl | cyclopropyloxy |
| 54 | cyclobutyloxy | cyclopentyloxy |
| 55 | cyclohexyloxy | cycloheptyloxy |
| 56 | OCH$_2$-cyclopropyl | OCH$_2$-cyclopentyl |
| 57 | OCH$_2$C(Cl)=CH$_2$ | OCH$_2$C=C—Br |
| 58 | OCH$_2$CH=C(Cl)$_2$ | OCH$_2$C(Br)=CH$_2$ |

TABLE 3

$R^1$=2'-F, $R^2$=6'-F, $R^4$=$R^5$=H, $R^3$=

| | COLUMN 1 | COLUMN 2 | COLUMN 3 |
|---|---|---|---|
| 59 | 2-CN—Ph | 2-benzothienyl | C≡C(2-CF$_3$—Ph) |
| 60 | 3-CN—Ph | 3-benzothienyl | C≡C(3-CF$_3$—Ph) |
| 61 | 4-CN—Ph | 5-benzothienyl | C≡C(2-CH$_3$—Ph) |
| 62 | 4-NO$_2$—Ph | 5-benzodioxolyl | C≡C(3-CH$_3$—Ph) |
| 63 | 4-SF$_5$—Ph | 2-benzoxazolyl | C≡C(4-CH$_3$—Ph) |
| 64 | 4-SMe—Ph | 5-benzoxazolyl | C≡C(2-OMe—Ph) |
| 65 | 4-SEt—Ph | 6-chromanyl | C≡C(3-OMe—Ph) |
| 66 | SCF$_3$—Ph | 1-Me-3-indolinyl | C≡C(4-OMe—Ph) |
| 67 | 4-CO$_2$Me—Ph | 6-benzodioxanyl | C≡C(4-SMe—Ph) |
| 68 | 4-CO$_2$Et—Ph | 4-indanyl | C≡C(4-CN—Ph) |

TABLE 3-continued $R^1=2'-F, R^2=6'-F, R^4=R^5=H, R^3=$

| | COLUMN 1 | COLUMN 2 | COLUMN 3 |
|---|---|---|---|
| 69 | 4-C(O)CH$_3$—Ph | 5-indanyl | C≡C(3-CN—Ph) |
| 70 | 4-CHO—Ph | C≡C—Ph | C≡C(4-C(O)CH$_3$—Ph) |
| 71 | 1-naphthyl | C≡C(4-F—Ph) | C≡C(4-SF$_5$—Ph) |
| 72 | 6-Cl-2-naphthyl | C≡C(3-F—Ph) | C≡C(3-Br—Ph) |
| 73 | 6-tetralinyl | C≡C(2-F—Ph) | C≡C(4-Br—Ph) |
| 74 | 5-tetralinyl | C≡C(4-Cl—Ph) | C≡C(2,4-di-F—Ph) |
| 75 | 2-quinolyl | C≡C(4-CF$_3$—Ph) | C≡C(3,5-di-F—Ph) |
| 76 | 3-quinolyl | C(O)(4-F—Ph) | C≡C(3,4-di-F—Ph) |
| 77 | 1-isoquinolyl | C(O)(3-F—Ph) | C≡C(3,5-di-Cl—Ph) |
| 78 | 3-isoquinolyl | C(O)(2-F—Ph) | C≡C-(3,4-di-Cl—Ph) |
| 79 | 2-quinoxalinyl | CH=CH(4-F—Ph) | C≡C(3-OCF$_2$H—Ph) |
| 80 | 6-quinoxalinyl | CH=CH(3-F—Ph) | C≡C(4-OCF$_2$H—Ph) |
| 81 | 2-benzofuranyl | CH=CH(2-F—Ph) | C≡C(4-OCF$_3$—Ph) |
| 82 | 3-benzofuranyl | CH=CH(4-Cl—Ph) | C≡C(4-OCH$_2$CF$_3$—Ph) |
| 83 | 5-benzofuranyl | CH=CH—Ph | C≡C(2-CN—Ph) |
| 84 | 6-benzofuranyl | CH=CH(4-CF$_3$—Ph) | C≡C(2-F,4-Cl—Ph) |
| 85 | C≡C(2,4-di-Cl—Ph) | CH=CH(2-Cl—Ph) | C≡C(4-NO$_2$—Ph) |

TABLE 4

$R^1=2'-Cl, R^2=6'-F, R^4=R^5=H, R^3=$

| | COLUMN 1 | COLUMN 2 | COLUMN 3 |
|---|---|---|---|
| 86 | 2-CN—Ph | 2-benzothienyl | C≡C(2-CF$_3$—Ph) |
| 87 | 3-CN—Ph | 3-benzothienyl | C≡C(3-CF$_3$—Ph) |
| 88 | 4-CN—Ph | 5-benzothienyl | C≡C(2-CH$_3$—Ph) |
| 89 | 4-NO$_2$—Ph | 5-benzodioxolyl | C≡C(3-CH$_3$—Ph) |
| 90 | 4-SF$_5$—Ph | 2-benzoxazolyl | C≡C(4-CH$_3$—Ph) |
| 91 | 4-SMe—Ph | 5-benzoxazolyl | C≡C(2-OMe—Ph) |
| 92 | 4-SEt—Ph | 6-chromanyl | C≡C(3-OMe—Ph) |
| 93 | 4-SCF$_3$—Ph | 1-Me-3-indolinyl | C≡C(4-OMe—Ph) |
| 94 | 4-CO$_2$Me—Ph | 6-benzodioxanyl | C≡C(4-SMe—Ph) |
| 95 | 4-CO$_2$Et—Ph | 4-indanyl | C≡C(4-CN—Ph) |
| 96 | 4-C(O)CH$_3$—Ph | 5-indanyl | C≡C(3-CN—Ph) |
| 97 | 4-CHO—Ph | C≡C—Ph | C≡C(4-C(O)CH$_3$—Ph) |
| 98 | 1-naphthyl | C≡C(4-F—Ph) | C≡C(4-SF$_5$—Ph) |
| 99 | 6-Cl-2-naphthyl | C≡C(3-F—Ph) | C≡C(3-Br—Ph) |
| 100 | 6-tetralinyl | C≡C(2-F—Ph) | C≡C(4-Br—Ph) |
| 101 | 5-tetralinyl | C≡C(4-Cl—Ph) | C≡C(2,4-di-F—Ph) |
| 102 | 2-quinolyl | C≡C(4-CF$_3$—Ph) | C≡C(3,5-di-F—Ph) |
| 103 | 3-quinolyl | C(O)(4-F—Ph) | C≡C(3,4-di-F—Ph) |
| 104 | 1-isoquinolyl | C(O)(3-F—Ph) | C≡C(3,5-di-Cl—Ph) |
| 105 | 3-isoquinolyl | C(O)(2-F—Ph) | C≡C(3,4-di-Cl—Ph) |
| 106 | 2-quinoxalinyl | CH=CH(4-F—Ph) | C≡C(3-OCF$_2$H—Ph) |
| 107 | 6-quinoxalinyl | CH=CH(3-F—Ph) | C≡C(4-OCF$_2$H—Ph) |
| 108 | 2-benzofuranyl | CH=CH(2-F—Ph) | C≡C(4-OCF$_3$—Ph) |
| 109 | 3-benzofuranyl | CH=CH(4-Cl—Ph) | C≡C(4-OCH$_2$CF$_3$—Ph) |
| 110 | 5-benzofuranyl | CH=CH—Ph | C≡C(2-CN—Ph) |
| 111 | 6-benzofuranyl | CH=CH(4-CF$_3$—Ph) | C≡C(2-F,4-Cl—Ph) |
| 112 | C≡C(2,4-di-Cl—Ph) | CH=CH(2-Cl—Ph) | C≡C(4-NO$_2$—Ph) |

TABLE 5

$R^1=2'-F, R^4=H, R^5=H$

| | COLUMN 1 | | COLUMN 2 | |
|---|---|---|---|---|
| | $R^2=$ | $R^3=$ | $R^2=$ | $R^3=$ |
| 113 | H | C≡C(4-F—Ph) | 6'-Cl | C≡C(4-F—Ph) |
| 114 | H | C≡C(4-Cl—Ph) | 6'-Cl | C≡C(4-Cl—Ph) |
| 115 | H | C≡C(2,4-di-Cl—Ph) | 6'-Cl | C≡C(2,4-di-Cl—Ph) |
| 116 | H | C≡C(Ph) | 6'-Cl | C≡C(Ph) |
| 117 | H | 4-CN—Ph | 6'-Cl | 4-CN—Ph |
| 118 | H | 4-SCF$_3$—Ph | 6'-Cl | 4-SCF$_3$—Ph |
| 119 | H | CH=CH(4-F—Ph) | 6'-Cl | CH=CH(4-F—Ph) |
| 120 | H | CH=CH(4-Cl—Ph) | 6'-Cl | CH=CH(4-Cl—Ph) |
| 121 | H | CH=CH(4-CF$_3$—Ph) | 6'-Cl | CH=CH(4-CF$_3$—Ph) |

$R^1=2'-F, R^2=6'-F, R^4=3-Cl$

| | COLUMN 1 | | COLUMN 2 | |
|---|---|---|---|---|
| | $R^5=$ | $R^3=$ | $R^5=$ | $R^3=$ |
| 122 | H | C≡C(4-F—Ph) | 5-Cl | C≡C(4-F—Ph) |
| 123 | H | C≡C(4-Cl—Ph) | 5-Cl | C≡C(4-Cl—Ph) |
| 124 | H | C≡C(2,4-di-Cl—Ph) | 5-Cl | C≡C(2,4-di-Cl—Ph) |
| 125 | H | 4-CN—Ph | 5-Cl | 4-CN—Ph |
| 126 | H | 4-SCF$_3$—Ph | 5-Cl | 4-SCF$_3$—Ph |
| 127 | H | C≡C(2,4-di-F—Ph) | 5-Cl | C≡C(2,4-di-F—Ph) |
| 128 | H | C≡C(2-F,4-Cl—Ph) | 5-Cl | C≡C(2-F,4-Cl—Ph) |
| 129 | H | 4-SMe—Ph | 5-Cl | 4-SMe—Ph |
| 130 | H | 2-naphthyl | 5-Cl | 2-naphthyl |

$R^1=2'-Cl, R^2=H, R^4=H, R^5=H, R^3=$

COLUMN 1

| 131 | C≡C(4-F—Ph) |
|---|---|
| 132 | CH=CH(4-F—Ph) |

Formulation/Utility

The present invention further comprises agricultural compositions containing one or more compounds of Formula I as previously defined. Compounds of this invention will generally be used in formulation with an agriculturally suitable carrier comprising a liquid or solid diluent. Useful formulations include dusts, granules, baits, pellets, solutions, suspensions, emulsions, wettable powders, emulsifiable concentrates, dry flowables and the like, consistent with the physical properties of the active ingredient, mode of application and environmental factors such as soil type, moisture and temperature. Sprayable formulations can be extended in suitable media and used at spray volumes from about one to several hundred liters per hectare. High strength compositions are primarily used as intermediates for further formulation. The formulations will typically contain effective amounts of active ingredient, diluent and surfactant within the following approximate ranges which add up 100 weight percent.

| | Weight Percent | | |
|---|---|---|---|
| | Active Ingredient | Diluent | Surfactant |
| Wettable Powders | 5–90 | 0–74 | 1–10 |
| Oil Suspensions, Emulsions, Solutions, (including Emulsifiable Concentrates) | 5–50 | 40–95 | 0–15 |
| Dusts | 1–25 | 70–99 | 0–5 |
| Granules, Baits and Pellets | 0.01–99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Doffand Books, Caldwell, N.J. Typical liquid diluents and solvents are described in Marsden, *Solvents Guide*, 2nd Ed., Interscience, New York, 1950. *McCutcheon's Detergents and Emulsifiers Annual*, Allured Publ. Corp., Ridgewood, N.J., as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth, and the like.

Solutions are prepared by simply mixing the ingredients. Fine solid compositions are made by blending and, usually, grinding as in a hammer mill or fluid energy mill. Water-dispersible granules can be produced by agglomerating a fine powder composition; see for example, Cross et al., *Pesticide Formulations*, Washington, D.C., 1988, pp 251–259. Suspensions are prepared by wet-milling; see, for example, U.S. Pat. No. 3,060,084. Granules and pellets can be made by spraying the active material upon preformed granular carriers or by agglomeration techniques. See Browning, "Agglomeration", *Chemical Engineering*, December 4, 1967, pp 147–148, Perry's *Chemical Engineer's Handbook*, 4th Ed., McGraw-Hill, New York, 1963, pages 8–57 and following, and WO 91/13546.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Tables A and B.

Example A

Wettable Powder

| | |
|---|---|
| Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |

Example B

Granule

| | |
|---|---|
| Compound 1 | 10.0% |
| attapulgite granules (low volatile matter, 0.71/0.30 mm; U.S.S. No. 25–50 sieves) | 90.0%. |

Example C

Extruded Pellet

| | |
|---|---|
| Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Example D

Emulsifiable Concentrate

| | |
|---|---|
| Compound 1 | 20.0% |
| blend of oil soluble sulfonates and polyoxyethylene ethers | 10.0% |
| isophorone | 70.0%. |

The compounds of this invention exhibit activity against a wide spectrum of foliar-feeding, fruit-feeding, stem or root feeding, seed-feeding, aquatic and soil-inhabiting arthropods (term "arthropods" includes insects, mites and nematodes) which are pests of growing and stored agronomic crops, forestry, greenhouse crops, ornamentals, nursery crops, stored food and fiber products, livestock, household, and public and animal health. Those skilled in the art will appreciate that not all compounds are equally effective against all growth stages of all pests. Nevertheless, all of the compounds of this invention display activity against pests that include: eggs, larvae and adults of the Order Lepidoptera; eggs, foliar-feeding, fruit-feeding, root-feeding, seed-feeding larvae and adults of the Order Coleoptera; eggs, immatures and adults of the Orders Hemiptera and Homoptera; eggs, larvae, nymphs and adults of the Order Acari; eggs, immatures and adults of the Orders Thysanoptera, Orthoptera and Dermaptera; eggs, immatures and adults of the Order Diptera; and eggs, junveniles and adults of the Phylum Nematoda. The compounds of this invention are also active against pests of the Orders Hymenoptera, Isoptera, Siphonaptera, Blattaria, Thysanura and Psocoptera; pests belonging to the Class Arachnida and Phylum Platyhelminthes. Specifically, the compounds are active against southern corn rootworm (*Diabrotica undecimpunctata howardi*), aster leafhopper (*Mascrosteles fascifrons*), boll weevil (*Anthonomus grandis*), two-spotted spider mite (*Tetranychus urticae*), fall armyworm (*Spodoptera frugiperda*), black bean aphid (*Aphis fabae*), green peach aphid (*Myzus persica*), cotton aphid (*Aphis gossypii*), Russian wheat aphid (*Diuraphis noxia*), English grain aphid (*Sitobion avenae*), tobacco budworm (*Hellothis virescens*), rice water weevil (*Lissorhoptrus oryzophilus*), rice leaf beetle (*Oulema oryzae*), whitebacked planthopper (*Sogatella furcifera*), green leafhopper (*Nephotettix cincticeps*), brown planthopper (*Nilaparvata lugens*), small brown planthopper (*Laodelphax striatellus*), rice stem borer (*Chilo suppressalis*), rice leafroller (*Cnaphalocrocis medinalis*), black rice stink bug (*Scotinophara lurida*), rice stink bug (*Oebalus pugnax*), rice bug (*Leptocorisa chinensis*), slender rice bug (*Cletus puntiger*), and southern green stink bug (*Nezara viridula*). The compounds are active on mites, demonstrating ovicidal, larvicidal and chemosterilant activity against such families as Tetranychidae including *Tetranychus urticae, Tetranychus cinnabarinus, Tetranychus mcdanieli, Tetranychus pacificus, Tetranychus turkestani, Byrobia rubrioculus, Panonychus ulmi, Panonychus citri, Eotetranychus carpini borealis, Eotetranychus, hicoriae, Eotetranychus sexmaculatus, Eotetranychus yumensis, Eotetranychus banksi* and *Oligonychus pratensis;* Tenuipalpidae including *Brevipalpus lewisi, Brevipalpus phoenicis, Brevipalpus californicus and Brevipalpus obovatus;* Eriophyidae including *Phyllocoptruta oleivora, Eriophyes sheldoni, Aculus cornutus, Epitrimerus pyri* and *Eriophyes mangiferae*. See WO 90/10623 and WO 92/00673 for more detailed pest descriptions.

Compounds of this invention can also be mixed with one or more other insecticides, fungicides, nematocides, bactericides, acaricides, growth regulators, chemosterilants, semiochemicals, repellants, attractants, pheromones, feeding stimulants or other biologically active compounds to form a multi-component pesticide giving an even broader spectrum of agricultural protection. Examples of other agricultural protectants with which compounds of this invention can be formulated are: insecticides such as avermectin B, monocrotophos, carbofuran, tetrachlorvinphos, malathion, parathion-methyl, methomyl, chlordimeform, diazinon, dekamethrin, oxamyl, fenvalerate, esfenvalerate, permethrin, profenofos, sulprofos, triflumuron, diflubenzuron, methoprene, buprofezin, thiodicarb, acephate, azinphosmethyl, chlorpyrifos, dimethoate, fipronil, flufenprox, fonophos, isofenphos, methidathion, metha-midophos, phosmet, phosphamidon, phosalone, pirimicarb, phorate, terbufos, trichlorfon, methoxychlor, bifenthrin, biphenate, cyfluthrin, tefluthrin, fenpropathrin, fluvalinate, flucythrinate, tralomethrin, imidacloprid, metaldehyde and rotenone; fungicides such as carbendazim, thiuram, dodine, maneb, chloroneb, benomyl, cymoxanil, fenpropidine, fenpropimorph, triadimefon, captan, thiophanate-methyl, thiabendazole, phosethyl-Al, chlorothalonil, dichloran, metalaxyl, captafol, iprodione, oxadixyl, vinclozolin, kasugamycin, myclobutanil, tebuconazole, difenoconazole, diniconazole, fluquinconazole, ipconazole, metconazole, penconazole, propiconazole, uniconzole, flutriafol, prochloraz, pyrifenox, fenarimol, triadimenol, diclobutrazol, copper oxychloride, furalaxyl, folpet, flusilazol, blasticidin S, diclomezine, edifenphos, isoprothiolane, iprobenfos, mepronil, neo-asozin, pencycuron, probenazole, pyroquilon, tricyclazole, validamycin, and flutolanil; nematocides such as aldoxycarb, fenamiphos and fosthietan; bactericides such as oxytetracyline, streptomycin and tribasic copper sulfate; acaricides such as binapacryl, oxythioquinox, chlorobenzilate, dicofol, dienochlor, cyhexatin, hexythiazox, amitraz, propargite, tebufenpyrad and fenbutatin oxide; and biological agents such as entomopathogenic bacteria, virus and fungi.

In certain instances, combinations with other arthropodicides having a similiar spectrum of control but a different mode of action will be particularly advantageous for resistance management.

Arthropod pests are controlled and protection of agronomic, horticultural and specialty crops, animal and human health is achieved by applying one or more of the compounds of this invention, in an effective amount, to the environment of the pests including the agronomic and/or nonagronomic locus of infestation, to the area to be protected, or directly on the pests to be controlled. Thus, the present invention further comprises a method for the control of foliar and soil inhabiting arthropods and nematode pests and protection of agronomic and/or nonagronomic crops, comprising applying one or more of the compounds of Formula I, or compositions containing at least one such compound, in an effective amount, to the environment of the pests including the agronomic and/or nonagronomic locus of infestation, to the area to be protected, or directly on the pests to be controlled. A preferred method of application is by spraying. Alternatively, granular formulations of these compounds can be applied to the plant foliage or the soil. Other methods of application include direct and residual sprays, aerial sprays, seed coats, microencapsulations, systemic uptake, baits, eartags, boluses, foggers, fumigants, aerosols, dusts and many others. The compounds can be incorporated into baits that are consumed by the arthropods or in devices such as traps and the like.

The compounds of this invention can be applied in their pure state, but most often application will be of a formulation comprising one or more compounds with suitable carriers, diluents, and surfactants and possibly in combination with a food depending on the contemplated end use. A preferred method of application involves spraying a water dispersion or refined oil solution of the compounds. Combinations with spray oils, spray oil concentrations, spreader stickers, adjuvants, and synergists and other solvents such as piperonyl butoxide often enhance compound efficacy.

The rate of application required for effective control will depend on such factors as the species of arthropod to be controlled, the pest's life cycle, life stage, its size, location, time of year, host crop or animal, feeding behavior, mating behavior, ambient moisture, temperature, and the like. Under normal circumstances, application rates of about 0.01 to 2 kg of active ingredient per hectare are sufficient to control pests in agronomic ecosystems, but as little as 0.001 kg/hectare may be sufficient or as much as 8 kg hectare may be required. For nonagronomic applications, effective use rates will range from about 1.0 to 50 mg/square meter but as little as 0.1 mg/square meter may be sufficient or as much as 150 mg/square meter may be required.

The following TESTS demonstrate the control efficacy of compounds of this invention on specific pests. "Control efficacy" represents inhibition of arthropod development (including mortality) that causes significantly reduced feeding. The pest control protection afforded by the compounds is not limited, however, to these species. See Index Tables A and B for compound descriptions.

INDEX TABLE A

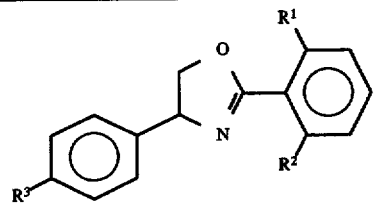

| Compound | R¹ | R² | R³ | Physical Properties (m.p. in °C.) |
|---|---|---|---|---|
| 1 | F | F | CO₂Et | oil (a) |
| 2 | F | F | cyclopentyloxy | oil (b) |
| 3 | F | F | tetrahydropyranyl | oil (c) |
| 4 | F | F | O(CH₂)₃CO₂Et | oil (d) |
| 5 | F | F | OCH(CH₃)CO₂Et | oil (e) |
| 6 | F | F | OCH₂(2-naphthyl) | 148–150 |
| 7 | F | F | OCH₂SiMe₃ | oil (f) |
| 8 | F | F | O-(2-benzoxazolyl) | oil (g) |
| 9 | F | F | O—CH₂cyclohexyl | oil (h) |
| 10 | F | F | O—(CH₂)₄CN | 82–84 |
| 11 | F | F | OCH₂C(Cl)=CH₂ | oil (i) |
| 12 | F | F | CH=CHPh | 109–110 |
| 13 | F | F | OCH₂CH=CCl₂ | 94–95 |
| 14 | F | F | 2-naphthyl | 166 |
| 15 | F | F | 4-CN—Ph | 135–136 |
| 16 | F | F | C(O)NH-(4-F—Ph) | 210–212 |
| 17 | F | F | 1-naphthyl | oil (j) |
| 18 | F | F | C(O)-4-F—Ph | 105–106 |
| 19 | F | F | C(O)-3-CF₃—Ph | oil (k) |
| 20 | F | F | C(O)Ph | oil (l) |
| 21 | F | F | C(O)-4-OMe—Ph | oil (m) |
| 22 | F | F | C≡C—Ph | oil (n) |
| 23 | F | F | CH=CH(4-F—Ph) | 154–156 |
| 24 | F | F | CH=CH(2-Cl—Ph) | oil (o) |
| 25 | F | F | 4-SMe—Ph | 162–163 |
| 26 | F | F | O-(6-Cl-2-quinoxalinyl) | 96–97 |
| 27 | F | F | O-(6-Cl-2-benzothiazolyl) | 80–82 |
| 28 | F | F | 4-CO₂Et—Ph | 73–76 |
| 29 | F | F | 4-CO₂Me—Ph | 124–125 |
| 30 | F | F | CH=CH(4-Cl—Ph) | 136–138 |
| 31 | F | F | C≡C(2-F,4-Cl—Ph) | wax (p) |
| 32 | F | F | CH=CH(3-Cl—Ph) | oil (q) |
| 33 | F | F | C≡C(4-F—Ph) | 107.5–108.5 |
| 34 | F | F | 4-CHO—Ph | 148–149 |
| 35 | F | F | C≡C(4-Cl—Ph) | 155–156 |
| 36 | F | F | C≡C(4-Br—Ph) | 166–168 |
| 37 | F | F | C≡C(4-OMe—Ph) | 108–110 |
| 38 | F | F | C≡C(2,4-di-Cl—Ph) | 90–91 |
| 39 | F | F | C≡C(3-CF₃—Ph) | oil (r) |
| 40 | F | F | C≡C(3-Cl—Ph) | oil (s) |

INDEX TABLE B

| Compound | R¹ | R² | R³ | Physical Properties (m.p. in °C.) |
|---|---|---|---|---|
| 41 | F | F | 2-(4-CN—Ph) | oil (t) |

¹H NMR data in CDCl₃ at 200 MHZ a) 8.0–7.0 (ArH), 5.5 (1H), 4.9 (1H), 4.4 (2H), 4.3 (1H), 1.4 (3H).

b) 7.3–6.9 (ArH), 5.4 (1H), 4.8 (2H), 4.3 (1H), 1.9–1.6 (8H).

c) 7.4–7.0 (m,7H), 5.4 (m,2H), 4.8 (m, 1H), 4.2 (m, 1H), 3.9 (m, 1H), 3.6 (m1H), 1.9–1.3 (m,6H).

d) 7.4–6.8 (m,7H), 5.4 (m, 1H), 4.8 (m, 1H), 4.2 (m, 1H), 4.1 (m,2H), 4.0 (m,2H), 2.6 (m,2H), 2.1 (m,2H), 1.2 (t,3H).

e) 7.2–6.8 (m,7H), 5.4 (m, 1H), 4.8 (m,2H), 4.2 (m,3H), 1.6 (d,3H), 1.2 (t,3H).

f) 7.6–6.9 (m,7H), 5.4 (m, 1H), 4.8 (m, 1H), 4.25 (m, 1H), 3.5 (m,2H), 0.1 (s,9H).

g) 7.6–7.0 (m, 11H), 5.5 (m, 1H), 4.8 (m, 1H), 4.3 (m, 1H).

h) 7.4–6.8 (m, 11H), 5.4 (m, 1H), 4.8 (m, 1H), 4.8 (m, 1H), 3.7 (m,2H)., 2.1–1.8 (m, 11H).

i) 7.4–6.9 (m,7H), 5.6–5.4 (m,3H), 4.8 (m, 1H), 4.6 (s,2H), 4.3 (m, 1H).

j) 7.9 (m,3H), 7.6 (m,9H), 7.0 (m,2H), 5.6 (m, 1H), 4.9 (m, 1H), 4.4 (m, 1H).

k) 8.1–7.0 (m, 11H), 5.6 (m, 1H), 4.9 (m, 1H), 4.3 (m, 1H).

l) 7.8–7.0 (m,12H), 5.6 (m, 1H), 4.9 (m, 1H), 4.3 (m, 1H).

m) 7.8–7.0 (m, 11H), 5.6 (m, 1H), 4.9 (m, 1H), 4.3 (m, 1H), 3.9 (s,3H).

n) 7.6–6.9 (m, 12H), 5.5 (m, 1H), 4.8 (m, 1H), 4.3 (m, 1H).

o) 7.7–6.9 (m, 13H), 5.5 (m, 1H), 4.8 (m, 1H), 4.3 (m, 1H).

p) 7.6–7.0 (m, 10H), 5.5 (1H), 4.8 (1H), 4.3 (1H).

q) 7.6–7.0 (m, 1H), 5.5 (1H), 4.8 (1H), 4.3 (1H).

r) 7.8–7.0 (m, 11H), 5.5 (1H), 4.8 (1H), 4.3 (1H).

s) 7.5–7.2 (m,9H), 7.0 (2H), 5.5 (1H), 4.8 (1H), 4.3 (1H).

t) 7.8–7.0 (m, 11H), 5.4 (1H), 4.4 (1H), 4.2 (1H).

TEST A

Fall Armyworm

Test units, each consisting of a H.I.S. (high impact styrene) tray with 16 cells were prepared. Wet filter paper and approximately 8 cm² of lima bean leaf is placed into twelve of the cells. A 0.5 cm layer of wheat germ diet is placed into the four remaining cells. Fifteen to twenty third-instar larvae of fall armyworm (*Spodoptera frugiperda*) were placed into an 8 ounce (230 mL) plastic cup. Solutions of each of the test compounds in 75/25 acetone/distilled water solvent were sprayed into the tray and cup. Spraying was accomplished by passing the tray and cup, on a conveyer belt, directly beneath a flat fan hydraulic nozzle which discharged the spray at a rate of 0.5 pounds of active ingredient per acre (about 0.55 kg/ha) at 30 p.s.i. (207 kPa). The insects were transferred from the 8 ounce cup into the cells of the H.I.S. tray (one insect per cell). The trays were covered and held at 27° C. and 50% relative humidity for 48 h after which time readings were taken on the twelve cells with lima bean leaves. The four remaining cells were read 7 days later for delayed toxicity readings. Of the compounds tested, the following gave control efficacy levels of 80% or higher: 6, 7, 8, 9, 12*, 14, and 15. * - tested at 250 ppm.

TEST B

Tobacco Budworm

The test procedure of TEST A was repeated for efficacy against third-instar larvae of the tobacco budworm (*Heliothis virescens*) except that three 8 ounce (230 mL) plastic cups with wheat germ diet were used in place of the H.I.S. tray, with each cup pre-infested with 5 third-instar larvae. Of the compounds tested, the following gave mortality levels of 80% or higher: 25.

TEST C

Larval two-Spotted Spider Mites (*Tetranychus urticae*)

Solutions of the test compounds were prepared by dissolving in a minimum of acetone and then adding water containing a wetting agent until the concentration of the compound was 50 ppm. Two-week old red kidney bean plants infested with two-spotted spider mites eggs were sprayed to run-off with the test solution using a turntable sprayer. Plants were held in a chamber at 25° C. and 50% relative humidity. Of the compounds tested, the following gave mortality levels of 80% or higher seven days after spraying: 1, 2, 3, 4, 5, 6, 7, 9, 10, 11, 12, 13, 14, 15, 17, 18, 25, 26, 27, 29, 30, 31, 33, 35, 36, 37, 38, 39, 40 and 41.

TEST D

Fall Armyworm Whole Plant Test

Solutions of the test compounds were prepared by dissolving in a minimum of acetone and adding water containing a wetting agent until the concentration of the compounds was 30 ppm. Test compounds were then sprayed to run-off onto soybean plants utilizing a rotating platform and an atomizing sprayer. Treated plants were dried, and fall armyworm (*Spodoptera frugiperda*) larvae were exposed to excised, treated leaves. Test units were held at 27° C. and 50% relative humidity, and evaluated for larval mortality 120 h post-infestation. Of the compounds tested, the following gave mortality levels of 80% or higher: 6, 12, 14, 15, 22, 23, 24, 25, 26, 29, 30, 31, 32, 33, 35, 36, 37, 38, 39 and 40.

We claim:

1. A compound of the formula wherein:

E is selected from the group $C_1$–$C_4$ alkyl and $C_1$–$C_4$ haloalkyl;

Z is selected from the group O and S;

$R^1$ is selected from the group F and Cl;

$R^2$ is selected from the group H, F and Cl;

$R^3$ is selected from the group $C_2$–$C_{10}$ alkynyl optionally substituted with at least one member independently selected from $R^9$; $OR^{12}$; phenyl substituted with at least one member independently selected from $W^1$; and an 8- to 12-membered fused bicyclic ring system containing 0–4 heteroatoms independently selected from 0–4 nitrogen, 0–2 oxygen and 0–2 sulfur, the ring system optionally substituted with at least one member independently selected from W;

$R^4$ and $R^5$ are independently selected from the group H, halogen, CN, $NO_2$, $C_1$–$C_{16}$ alkyl, $C_1$–$C_{16}$ alkoxy, $C_1$–$C_{16}$ haloalkyl, $C_1$–$C_{16}$ haloalkoxy, $C_3$–$C_7$ cycloalkyl, $C_4$–$C_{16}$ cycloalkylalkyl, $C_2$–$C_{16}$ alkenyl, $C_2$–$C_{16}$ haloalkenyl, $C_2$–$C_{16}$ alkynyl, $C_2$–$C_{16}$ haloalkynyl, $C_2$–$C_{16}$ alkoxyalkoxy, $Si(R^6)(R^7)R^8$, and phenyl optionally substituted with at least one member independently selected from W;

$R^6$, $R^7$ and $R^8$ are independently selected from $C_1$–$C_6$ alkyl;

$R^9$ is selected from the group phenyl and pyridyl, each optionally substituted with at least one member independently selected from W;

$R^{12}$ is selected from the group tetrahydropyranyl; $C_1$–$C_{10}$ alkyl substituted with at least one member independently selected from the group CN, $C_2$–$C_6$ alkylcarbonyl, $C_2$–$C_6$ haloalkylcarbonyl, $C_2$–$C_6$ haloalkoxycarbonyl, $C_2$–$C_6$ alkoxycarbonyl, $C_2$–$C_6$ alkylcarbonyl, and $Si(R^6)(R^7)R^8$; $C_3$–$C_7$ cycloalkyl; $C_3$–$C_7$ halocycloalkyl; $C_3$–$C_7$ cyanocycloalkyl; $C_4$–$C_7$ alkylcycloalkyl; $C_4$–$C_7$ cycloalkylalkyl; $C_4$–$C_7$ halocycloalkylalkyl; $C_3$–$C_{10}$ haloalkynyl; $C_2$–$C_{10}$ haloalkenyl optionally substituted with at least one member independently selected from the group CN and $C_2$–$C_6$ alkoxycarbonyl; and an 8- to 12-membered fused bicyclic ring system containing 0–4 heteroatoms independently selected from 0–4 nitrogen, 0–2 oxygen and 0–2 sulfur, the ring system optionally substituted with at least one member independently selected from W;

$R^{13}$ is selected from the group $C_1$–$C_3$ alkyl and $C_1$–$C_3$ haloalkyl;

W is selected from the group halogen, CN, CHO, $NO_2$, $SF_5$, $C_1$–$C_3$ alkyl, $C_1$–$C_3$ haloalkyl, $C_1$–$C_3$ alkylthio, $C_1$–$C_3$ alkoxy, $C_1$–$C_3$ haloalkoxy, $C_2$–$C_4$ alkylcarbonyl and $C_2$–$C_4$ alkoxycarbonyl;

$W^1$ is selected from the group CN, CHO, $NO_2$, $SF_5$, $S(O)_nR^{13}$, $C_2$–$C_4$ alkylcarbonyl, and $C_2$–$C_4$ alkoxycarbonyl;

n is 0, 1 or 2; and q is 0, 1, 2 or 3.

2. A compound according to claim 1 wherein:

$R^3$ is $OR^{12}$; and $R^{12}$ is $C_3$–$C_7$ cycloalkyl.

3. A compound according to claim 1 wherein:

$R^3$ is $C_2$–$C_{10}$ alkynyl optionally substituted with at least one member independently selected from $R^9$.

4. A compound according to claim 1 wherein:

$R^3$ is phenyl substituted with at least one member independently selected from $W^1$.

5. A compound according to claim 1 wherein:

$R^3$ is an 8- to 12-membered fused bicyclic ring system containing 0–4 heteroatoms independently selected from 0–4 nitrogen, 0–2 oxygen and 0–2 sulfur, the ring system optionally substituted with at least one member independently selected from W.

6. A compound according to claim 1 selected from the group:

4'-((2-(2,6-difluorophenyl)-4,5-dihydro-4-oxazolyl))((1,1'-biphenyl))-4-carbonitrile; and 2-(2,6-difluorophenyl)-4,5-dihydro-4-[4-(2-naphthalenyl)phenyl]oxazole.

7. An optically active compound according to claim 1.

8. An arthropodicidal composition comprising an arthropodicidally effective amount of a compound according to claim 1 and a carrier therefor.

9. An arthropodicidal composition comprising an arthropodicidally effective amount of a compound of the formula

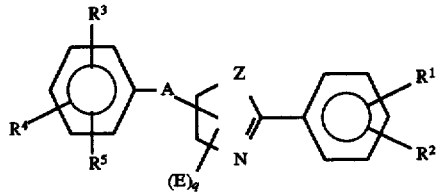

wherein:

A is selected from the group a direct bond and $C_1$–$C_3$ straight or branched chain alkylene;

E is selected from the group $C_1$–$C_4$ alkyl and $C_1$–$C_4$ haloalkyl;

Z is selected from the group O and S;

$R^1$ and $R^2$ are independently selected from the group H, halogen, $C_1$–$C_6$ alkyl, $C_1$–$C_6$ haloalkyl, $C_1$–$C_6$ haloalkoxy, $C_1$–$C_6$ alkylthio, CN and $NO_2$;

$R^3$ is selected from the group $C_3$–$C_7$ halocycloalkyl; $C_2$–$C_{10}$ haloalkenyl optionally substituted with a group selected from CN and $C_2$–$C_6$ alkoxycarbonyl; $C_1$–$C_{10}$ alkyl substituted with at least one member independently selected from the group $Si(R^6)(R^7)R^8$, CN, $C_2$–$C_6$ alkylcarbonyl, $C_2$–$C_6$ haloalkylcarbonyl, $C_2$–$C_6$ haloalkoxycarbonyl, and $C_2$–$C_6$ alkoxycarbonyl; $C_2$–$C_6$ alkylcarbonyl; $C_2$–$C_{10}$ alkenyl optionally substituted with at least one member independently selected from $R^9$; $C_2$–$C_{10}$ alkynyl optionally substituted with at least one member independently selected from $R^9$; $C_2$–$C_6$ haloalkylcarbonyl; $C_2$–$C_6$ alkoxycarbonyl; $C_2$–$C_6$ haloalkoxycarbonyl; $C(O)R^9$; $C(O)OR^9$; $C(O)N(R^{10})R^{11}$; $OR^{12}$; tetrahydropyranyl; phenyl substituted with at least one member independently selected from $W^1$; and an 8- to 12-membered fused bicyclic ring system containing 0–4 heteroatoms independently selected from 0–4 nitrogen, 0–2 oxygen and 0–2 sulfur, the ring system optionally substituted with at least one member independently selected from W;

$R^4$ and $R^5$ are independently selected from the group H, halogen, CN, $NO_2$, $C_1$–$C_{16}$ alkyl, $C_1$–$C_{16}$ alkoxy, $C_1$–$C_{16}$ haloalkyl, $C_1$–$C_{16}$ haloalkoxy, $C_3$–$C_7$ cycloalkyl, $C_4$–$C_{16}$ cycloalkylalkyl, $C_2$–$C_{16}$ alkenyl, $C_2$–$C_{16}$ haloalkenyl, $C_2$–$C_{16}$ alkynyl, $C_2$–$C_{16}$ haloalkynyl, C2-C16 alkoxyalkoxy, $Si(R^6)CR^7)R^8$, and phenyl optionally substituted with at least one member independently selected from W;

$R^6$, $R^7$ and $R^8$ are independently selected from $C_1$–$C_6$ alkyl;

$R^9$ is selected from the group phenyl and pyridyl, each optionally substituted with at least one member independently selected from W;

$R^{10}$ and $R^{11}$ are independently selected from the group H, $C_1$–$C_6$ alkyl, $C_1$–$C_6$ haloalkyl, and phenyl optionally substituted with at least one member independently selected from W;

$R^{12}$ is selected from the group tetrahydropyranyl; $C_1$–$C_{10}$ alkyl substituted with at least one member independently selected from the group CN, $C_2$–$C_6$ alkylcarbonyl, $C_2$–$C_6$ haloalkylcarbonyl, $C_2$–$C_6$ haloalkoxycarbonyl, $C_2$–$C_6$ alkoxycarbonyl, $C_2$–$C_6$ alkylcarbonyl, and Si($R^6$)($R^7$)$R^8$; $C_3$–$C_7$ cycloalkyl; $C_3$–$C_7$ halocycloalkyl; $C_3$–$C_7$ cyanocycloalkyl; $C_4$–$C_7$ alkylcycloalkyl; $C_4$–$C_7$ cycloalkylalkyl; $C_4$–$C_7$ halocycloalkylalkyl; $C_3$–$C_{10}$ haloalkynyl; $C_2$–$C_{10}$ haloalkenyl optionally substituted with at least one member independently selected from the group CN and $C_2$–$C_6$ alkoxycarbonyl; and an 8- to 12-membered fused bicyclic ring system containing 0–4 heteroatoms independently selected from 0–4 nitrogen, 0–2 oxygen and 0–2 sulfur, the ring system optionally substituted with at least one member independently selected from W;

$R^{13}$ is selected from the group $C_1$–$C_3$ alkyl and $C_1$–$C_3$ haloalkyl;

W is selected from the group halogen, CN, CHO, $NO_2$, $SF_5$, $C_1$–$C_3$ alkyl, $C_1$–$C_3$ haloalkyl, $C_1$–$C_3$ alkylthio, $C_1$–$C_3$ alkoxy, $C_1$–$C_3$ haloalkoxy, $C_2$–$C_4$ alkylcarbonyl and $C_2$–$C_4$ alkoxycarbonyl;

$W^1$ is selected from the group CN, CHO, $NO_2$, $SF_5$, $S(O)_n R^{13}$, $C_2$–$C_4$ alkylcarbonyl, and $C_2$–$C_4$ alkoxycarbonyl;

n is 0, 1 or 2; and q is 0, 1, 2 or 3;

and a carrier therefor.

10. A method for controlling arthropods comprising contacting the arthropods or their environment with an arthropodicidally effective mount of a compound according to claim 1.

11. A method for controlling arthropods comprising contacting the arthropods or their environment with an arthropodicidally effective amount of a compound of the formula

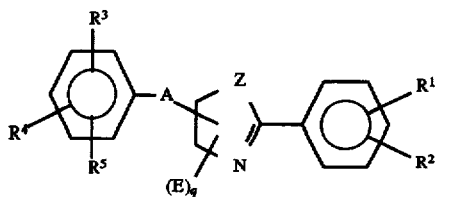

wherein:

A is selected from the group a direct bond and $C_1$–$C_3$ straight or branched chain alkylene;

E is selected from the group $C_1$–$C_4$ alkyl and $C_1$–$C_4$ haloalkyl;

Z is selected from the group O and S;

$R^1$ and $R^2$ are independently selected from the group H, halogen, $C_1$–$C_6$ alkyl, $C_1$–$C_6$ haloalkyl, $C_1$–$C_6$ haloalkoxy, $C_1$–$C_6$ alkylthio, CN and $NO_2$;

$R^3$ is selected from the group $C_3$–$C_7$ halocycloalkyl; $C_2$–$C_{10}$ haloalkenyl optionally substituted with a group selected from CN and $C_2$–$C_6$ alkoxycarbonyl; $C_1$–$C_{10}$ alkyl substituted with at least one member independently selected from the group Si($R^6$)($R^7$)$R^8$, CN, $C_2$–$C_6$ alkylcarbonyl, $C_2$–$C_6$ haloalkylcarbonyl, $C_2$–$C_6$ haloalkoxycarbonyl, and $C_2$–$C_6$ alkoxycarbonyl; $C_2$–$C_6$ alkyl carbonyl; $C_2$–$C_{10}$ alkenyl optionally substituted with at least one member independently selected from $R^9$; $C_2$–$C_{10}$ alkynyl optionally substituted with at least one member independently selected from $R^9$; $C_2$–$C_6$ haloalkylcarbonyl; $C_2$–$C_6$ alkoxycarbonyl; $C_2$–$C_6$ haloalkoxycarbonyl; C(O)$R^9$; C(O)O$R^9$; C(O)N($R^{10}$)$R^{11}$; O$R^{12}$; tetrahydropyranyl; phenyl substituted with at least one member independently selected from $W^1$; and an 8- to 12-membered fused bicyclic ring system containing 0–4 heteroatoms independently selected from 0–4 nitrogen, 0–2 oxygen and 0–2 sulfur, the ring system optionally substituted with at least one member independently selected from W;

$R^4$ and $R^5$ are independently selected from the group H, halogen, CN, $NO_2$, $C_1$–$C_{16}$ alkyl, $C_1$–$C_{16}$ alkoxy, $C_1$–$C_{16}$ haloalkyl, $C_1$–$C_{16}$ haloalkoxy, $C_3$–$C_7$ cycloalkyl, $C_4$–$C_{16}$ cycloalkylalkyl, $C_2$–$C_{16}$ alkenyl, $C_2$–$C_{16}$ haloalkenyl, $C_2$–$C_{16}$ alkynyl, $C_2$–$C_{16}$ haloalkynyl, $C_2$–$C_{16}$ alkoxyalkoxy, Si($R^6$)($R^7$)$R^8$, and phenyl optionally substituted with at least one member independently selected from W;

$R^7$ and $R^8$ are independently selected from $C_1$–$C_6$ alkyl;

$R^9$ is selected from the group phenyl and pyridyl, each optionally substituted with at least one member independently selected from W;

$R^{10}$ and $R^{11}$ are independently selected from the group H, $C_1$–$C_6$ alkyl, $C_1$–$C_6$ haloalkyl, and phenyl optionally substituted with at least one member independently selected from W;

$R^{12}$ is selected from the group tetrahydropyranyl; $C_1$–$C_{10}$ alkyl substituted with at least one member independently selected from the group CN, $C_2$–$C_6$ alkylcarbonyl, $C_2$–$C_6$ haloalkylcarbonyl, $C_2$–$C_6$ haloalkoxycarbonyl, $C_2$–$C_6$ alkoxycarbonyl, $C_2$–$C_6$ alkylcarbonyl, and Si($R^6$)($R^7$)$R^8$; $C_3$–$C_7$ cycloalkyl; $C_3$–$C_7$ halocycloalkyl; $C_3$–$C_7$ cyanocycloalkyl; $C_4$–$C_7$ alkylcycloalkyl; $C_4$–$C_7$ cycloalkylalkyl; $C_4$–$C_7$ halocycloalkylalkyl; $C_3$–$C_{10}$ haloalkynyl; $C_2$–$C_{10}$ haloalkenyl optionally substituted with at least one member independently selected from the group CN and $C_2$–$C_6$ alkoxycarbonyl; and an 8- to 12-membered fused bicyclic ring system containing 0–4 heteroatoms independently selected from 0–4 nitrogen, 0–2 oxygen and 0–2 sulfur, the ring system optionally substituted with at least one member independently selected from W;

$R^{13}$ is selected from the group $C_1$–$C_3$ alkyl and $C_1$–$C_3$ haloalkyl;

W is selected from the group halogen, CN, CHO, $NO_2$, $SF_5$, $C_1$–$C_3$ alkyl, $C_1$–$C_3$ haloalkyl, $C_1$–$C_3$ alkylthio, $C_1$–$C_3$ alkoxy, $C_1$–$C_3$ haloalkoxy, $C_2$–$C_4$ alkylcarbonyl and $C_2$–$C_4$ alkoxycarbonyl;

$W^1$ is selected from the group CN, CHO, $NO_2$, $SF_5$, $S(O)_n R^{13}$, $C_2$–$C_4$ alkylcarbonyl, and $C_2$–$C_4$ alkoxycarbonyl;

n is 0, 1 or 2; and q is 0, 1, 2 or 3.

* * * * *

UNITED STATES PATENT AND TRADEMARK OFFICE
CERTIFICATE OF CORRECTION

PATENT NO. : 5,686,393
DATED : November 11, 1997
INVENTOR(S) : George Philip Lahm, et al.

It is certified that error appears in the above-identified patent and that said Letters Patent is hereby corrected as shown below:

Col. 1, line 53: delete "C(O)N" and substitute therefor -- C(O)N- --.

Col. 14, line 2: delete "with" and substitute therefor -- , and --.

Col. 25, line 53: delete "q is0, 1, 2or3." and substitute therefor -- q is 0, 1, 2 or 3. --

Col. 28, line 61: delete "q is0, 1, 2or3." and substitute therefor -- q is 0, 1, 2 or 3. --

Signed and Sealed this

Twenty-fourth Day of November, 1998

BRUCE LEHMAN

Attest:

Attesting Officer

Commissioner of Patents and Trademarks